(12) United States Patent
Stuebe

(10) Patent No.: US 8,840,609 B2
(45) Date of Patent: Sep. 23, 2014

(54) TISSUE FUSION SYSTEM AND METHOD OF PERFORMING A FUNCTIONAL VERIFICATION TEST

(75) Inventor: Brian C. Stuebe, Broomfield, CO (US)

(73) Assignee: Conmed Corporation, Utica, NY (US)

( * ) Notice: Subject to any disclaimer, the term of this patent is extended or adjusted under 35 U.S.C. 154(b) by 1004 days.

(21) Appl. No.: 12/842,659

(22) Filed: Jul. 23, 2010

(65) Prior Publication Data
US 2012/0022517 A1 Jan. 26, 2012

(51) Int. Cl.
*A61B 18/08* (2006.01)
*A61B 17/00* (2006.01)
*A61B 18/00* (2006.01)
*A61B 18/10* (2006.01)

(52) U.S. Cl.
CPC ..... *A61B 18/085* (2013.01); *A61B 2017/00725* (2013.01); *A61B 2018/0063* (2013.01); *A61B 2018/00666* (2013.01); *A61B 2017/00973* (2013.01); *A61B 18/10* (2013.01); *A61B 2018/00714* (2013.01); *A61B 2018/00791* (2013.01); *A61B 2017/00199* (2013.01); *A61B 2018/00892* (2013.01); *A61B 2018/00827* (2013.01); *A61B 2017/00123* (2013.01); *A61B 2018/00875* (2013.01); *A61B 2017/0003* (2013.01)
USPC ............................................. 606/31; 606/34

(58) Field of Classification Search
CPC ...... A61B 18/04; A61B 18/08; A61B 18/082; A61B 18/085; A61B 18/1442; A61B 18/1445; A61B 18/1447; A61B 2018/00827; A61B 2018/00648; A61B 2018/00654; A61B 2018/00892

USPC .................................. 606/33, 34, 41, 50–52
See application file for complete search history.

(56) References Cited

U.S. PATENT DOCUMENTS

| | | | |
|---|---|---|---|
| 3,662,151 A | 5/1972 | Haffey |
| 3,768,482 A | 10/1973 | Shaw |
| 3,826,263 A | 7/1974 | Cage et al. |
| 4,074,719 A | 2/1978 | Semm |
| RE30,190 E | 1/1980 | Shaw |
| 4,196,734 A | 4/1980 | Harris |
| 4,198,957 A | 4/1980 | Cage et al. |
| 4,207,896 A | 6/1980 | Shaw |
| 4,219,025 A | 8/1980 | Johnson |
| 4,231,371 A | 11/1980 | Lipp |

(Continued)

FOREIGN PATENT DOCUMENTS

| | | |
|---|---|---|
| EP | 0878168 A1 | 11/1998 |
| EP | 1810634 A1 | 7/2007 |
| EP | 1862137 A1 | 12/2007 |

OTHER PUBLICATIONS

European Patent Office, European Search Report and European Search Opinion for Application No. 11170058.9 (related to priority U.S. Appl. No. 12/842,659), dated Jan. 5, 2012, 8 pages.

(Continued)

*Primary Examiner* — Michael Peffley
*Assistant Examiner* — Khadijeh Vahdat

(57) ABSTRACT

A jaw heating element of a handpiece of a thermal tissue operating system is tested on an ongoing basis by supplying a test heater power signal to the jaw heating element between individual thermal tissue operations. Voltage and current through the jaw heating element is sensed and the resistance of the jaw heating element is calculated. If the calculated resistance is outside a range of predetermined acceptable values, an error condition is indicated.

3 Claims, 8 Drawing Sheets

(56) References Cited

U.S. PATENT DOCUMENTS

| | | |
|---|---|---|
| 4,461,951 A | 7/1984 | Luoma, II et al. |
| RE31,723 E | 11/1984 | Shaw |
| 4,744,359 A | 5/1988 | Hatta et al. |
| 4,759,362 A | 7/1988 | Taniguchi |
| 5,021,634 A | 6/1991 | Santoro et al. |
| 5,352,868 A | 10/1994 | Denen et al. |
| 5,369,247 A | 11/1994 | Doljack |
| 5,383,874 A | 1/1995 | Jackson et al. |
| 5,400,267 A | 3/1995 | Denen et al. |
| 5,425,375 A | 6/1995 | Chin et al. |
| 5,445,635 A | 8/1995 | Denen et al. |
| 5,484,400 A | 1/1996 | Edwards et al. |
| 5,609,560 A | 3/1997 | Ichikawa et al. |
| 5,651,780 A | 7/1997 | Jackson et al. |
| 5,707,369 A | 1/1998 | Vaitekunas et al. |
| 5,743,903 A | 4/1998 | Stern et al. |
| 5,755,715 A | 5/1998 | Stern et al. |
| 5,792,138 A | 8/1998 | Shipp |
| 5,817,093 A | 10/1998 | Williamson, IV et al. |
| 5,906,614 A | 5/1999 | Stern et al. |
| 5,971,980 A | 10/1999 | Sherman |
| 5,991,355 A | 11/1999 | Dahlke |
| 6,017,354 A | 1/2000 | Culp et al. |
| 6,139,546 A | 10/2000 | Koenig et al. |
| 6,162,217 A | 12/2000 | Kannenberg et al. |
| 6,235,027 B1 | 5/2001 | Herzon |
| 6,237,604 B1 | 5/2001 | Burnside et al. |
| 6,266,551 B1 | 7/2001 | Osadchy et al. |
| 6,295,330 B1 | 9/2001 | Skog et al. |
| 6,329,778 B1 | 12/2001 | Culp et al. |
| 6,387,092 B1 | 5/2002 | Burnside et al. |
| 6,464,689 B1 | 10/2002 | Qin et al. |
| 6,533,778 B2 | 3/2003 | Herzon |
| 6,578,579 B2 | 6/2003 | Burnside et al. |
| 6,611,793 B1 | 8/2003 | Burnside et al. |
| 6,651,669 B1 | 11/2003 | Burnside |
| 6,685,701 B2 | 2/2004 | Orszulak et al. |
| 6,695,837 B2 | 2/2004 | Howell |
| 6,726,683 B1 | 4/2004 | Shaw |
| 6,733,495 B1 | 5/2004 | Bek et al. |
| 6,740,085 B2 | 5/2004 | Hareyama et al. |
| 6,783,523 B2 | 8/2004 | Qin et al. |
| 6,790,206 B2 | 9/2004 | Panescu |
| 6,792,390 B1 | 9/2004 | Burnside et al. |
| 6,793,652 B1 | 9/2004 | Whitman et al. |
| 6,796,980 B2 | 9/2004 | Hall |
| 6,827,713 B2 | 12/2004 | Bek et al. |
| 6,846,309 B2 | 1/2005 | Whitman et al. |
| 6,899,538 B2 | 5/2005 | Matoba |
| 6,939,346 B2 | 9/2005 | Kannenberg et al. |
| 6,942,660 B2 | 9/2005 | Pantera et al. |
| 6,994,704 B2 | 2/2006 | Qin et al. |
| 7,033,351 B2 | 4/2006 | Howell |
| 7,048,687 B1 | 5/2006 | Reuss et al. |
| 7,108,694 B2 | 9/2006 | Miura et al. |
| 7,137,980 B2 | 11/2006 | Buysse et al. |
| 7,196,295 B2 | 3/2007 | Fennewald et al. |
| 7,226,447 B2 | 6/2007 | Uchida et al. |
| 7,255,694 B2 | 8/2007 | Keppel |
| 7,258,688 B1 | 8/2007 | Shah et al. |
| 7,300,435 B2 | 11/2007 | Wham et al. |
| 7,335,197 B2 | 2/2008 | Sage et al. |
| 7,364,578 B2 | 4/2008 | Francischelli et al. |
| 2001/0029369 A1 | 10/2001 | Kannenberg et al. |
| 2002/0052599 A1* | 5/2002 | Goble ............................ 606/40 |
| 2002/0082593 A1* | 6/2002 | Hareyama et al. .............. 606/38 |
| 2002/0183734 A1 | 12/2002 | Bommannan et al. |
| 2004/0172016 A1 | 9/2004 | Bek et al. |
| 2004/0267297 A1 | 12/2004 | Malackowski |
| 2005/0004564 A1 | 1/2005 | Wham et al. |
| 2005/0245909 A1 | 11/2005 | McCary et al. |
| 2006/0086363 A1 | 4/2006 | Qin et al. |
| 2006/0161054 A1 | 7/2006 | Reuss et al. |
| 2006/0293649 A1 | 12/2006 | Lorang et al. |
| 2007/0167941 A1 | 7/2007 | Hamel et al. |
| 2007/0260233 A1 | 11/2007 | Miura |

OTHER PUBLICATIONS

European Patent Office, European Search Report and European Search Opinion for Application No. 11170056.3 (related to priority U.S. Appl. No. 12/842,606), dated Nov. 8, 2011, 7 pages.

* cited by examiner

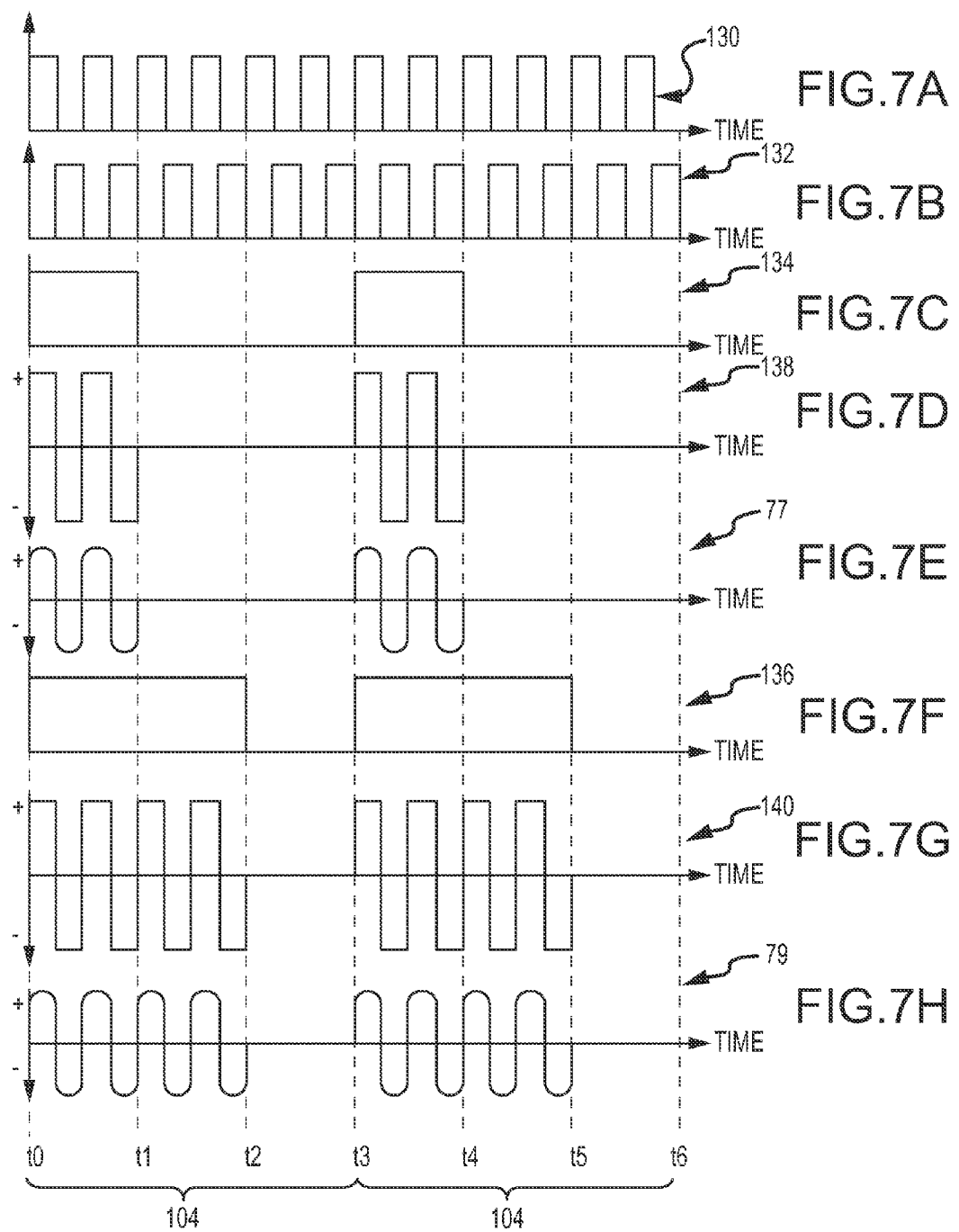

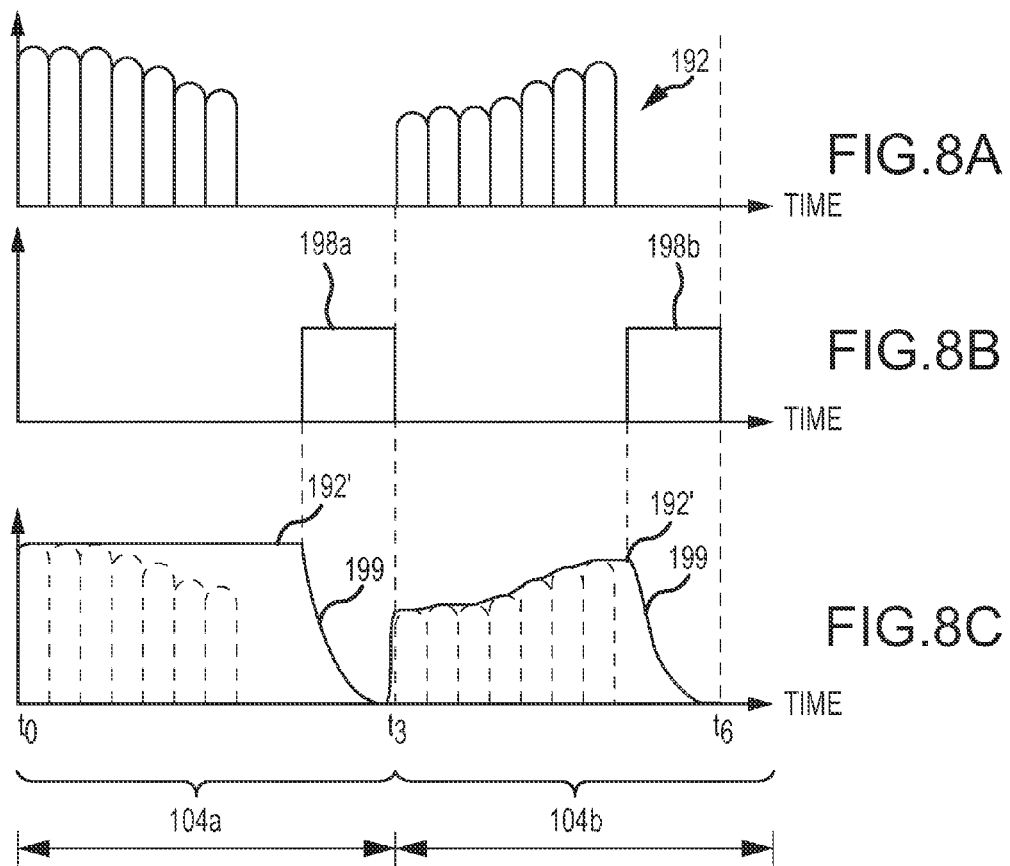
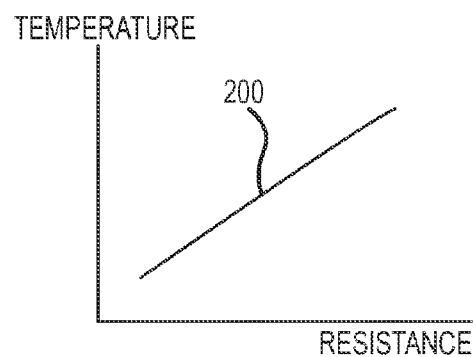
FIG.9

TISSUE FUSION SYSTEM AND METHOD OF PERFORMING A FUNCTIONAL VERIFICATION TEST

CROSS REFERENCE TO RELATED INVENTIONS

This invention is related to those inventions described in U.S. patent application Ser. No. 12/842,327 filed Jul. 23, 2010, titled Jaw Movement Mechanism and Method for Surgical Tool, and U.S. patent application Ser No. 12/842,399 filed Jul. 23, 2010, titled Surgical Tool and Method Using Crossbar Lever, and U.S. patent application Ser No. 12/842,606 filed Jul. 23, 2010, titled Tissue Fusion System and Method for Performing a Self Test, all of which are filed concurrently herewith and all of which are assigned to the assignee hereof. The subject matter of these applications is incorporated herein by this reference.

FIELD OF THE INVENTION

This invention relates to a thermal tissue operating system, which is also referred to generically as a tissue fusion system. More particularly, the present invention relates to a new and improved functional verification test in which jaw heating elements of a handpiece of the thermal tissue operating system are tested on a continuous basis during multiple, sequentially-occurring thermal tissue operations to identify potential problems and verify proper operation while the system is in use during a surgical procedure.

BACKGROUND OF THE INVENTION

A thermal tissue operation involves simultaneously compressing and heating tissue to seal together pieces of tissue, to cut a single piece of tissue into separate parts, or to sequentially seal pieces of tissue and then cut the sealed tissue. Tissue cutting occurs in the same manner as tissue sealing, except that additional energy and heat are applied to the tissue to cause it to sever. Typical thermal tissue operations involve sealing blood vessels during surgery to prevent bleeding and blood loss. Sealing a blood vessel before severing it between spaced apart sealed locations or in the middle of single sealed location completely avoids blood loss.

A thermal tissue operating system includes a handpiece which is connected to an energy source. The handpiece has a pair of opposing jaws between which the tissue is mechanically compressed. Electrical power from the energy source is converted to thermal heat energy in at least one of the opposing jaws, and the heat is conducted into the compressed tissue. The characteristics of the electrical energy applied to the jaws control the characteristics of the heat energy conducted into the jaws. The characteristics of the thermal energy transferred to the tissue and the time during which the thermal energy is transferred constitute an individual thermal tissue operation, i.e. a tissue sealing operation, a tissue cutting operation, or a combined tissue cutting and sealing operation. Usually, the entire surgical procedure is completed by performing many separate individual thermal tissue operations.

A thermal tissue operating system can be subject to a number of external influences, such as accidental mishandling and improper use, for example. Such external influences have the potential to adversely affect the proper operation of the system. A malfunctioning or improperly functioning system may inadequately seal tissue, inadequately cut tissue, inadequately seal and cut the tissue, and otherwise complicate the surgical procedure.

The jaw heating elements are subject to especially rigorous operating conditions. The jaw heating elements must conduct relatively high electrical current, must withstand rapidly increasing temperatures, must efficiently transfer thermal energy to the compressed tissue, and must maintain high temperature during the thermal tissue operation, among other things. When the thermal tissue operation is completed and electrical current is no longer conducted, the jaw heating elements undergo rapid cooling. The substantial changes in the electrical current conducted and the rapid increases and decreases in temperature impose significant stresses on the resistive material of the jaw heating elements and on the material surrounding the resistive material and on the adjoining structures and materials which support the jaw heating elements.

The cyclic nature of the energy application during repeated thermal tissue operations performed during the surgical procedure creates a practical limitation on the number of times that the heating elements will perform satisfactorily. For example, repeated use can cause the resistive material to undergo changes in properties or to develop areas of reduced or increased conductivity, resulting in changes in the resistance and thermal response characteristics of the jaw heating elements. As another example, an exaggerated temperature might melt the electrical connections to the jaw heating elements or even melt parts of the jaw heating elements or their supporting structures. Such adverse circumstances might cause an open circuit or short circuit condition to occur. Of course an open circuit prevents the jaw heating elements from conducting current and creating thermal energy. A short circuit might cause electrical current to flow into portions of the handpiece where it is not intended and could overload and therefore damage the energy source of the thermal tissue operating system.

A typical thermal tissue operating system employs feedback to regulate the amount of energy supplied to the jaw heating elements, thereby assuring that a desired temperature is applied or a desired amount of energy is transferred to the tissue compressed between the jaws. If the resistance of the jaw heating elements changes or if the current flow path to the heating elements changes in such a way to prevent or limit the maximum amount of current delivered to the jaw heating elements, the ability to regulate the temperature of the tissue compressed between the jaws will be impaired. Of course, impaired temperature regulation leads to degradation of the thermal tissue operation, because an insufficient or excessive amount of thermal energy will be applied to the compressed tissue.

In some cases where less than the desired amount of thermal energy is applied to the compressed tissue, it can be difficult or impossible for the surgeon to recognize that the thermal effect on the tissue is inadequate. For example, in the case of a vessel which carries blood or other body fluid, an attempt to seal the vessel with a moderately inadequate amount of thermal energy may create an effect which appears to the surgeon to be a sound tissue seal. The tissue effect may even withstand internal bodily blood or fluid pressure for some short amount of time, before beginning to leak or rupturing. The resulting internal bleeding or fluid loss will then require a resealing thermal tissue operation. If the resealing operation is performed during the course of the surgical procedure, the time to do so prolongs the entire surgical procedure and subjects the patient to additional trauma. If the internal bleeding or fluid loss is discovered after the initial surgical procedure has been completed, a second surgical procedure must be performed to gain access to the leak and seal it. Performing a second surgical procedure on the patient adds substantially to the trauma that the patient has already experienced.

It is desirable to identify potential problems with a thermal tissue operating system before it is used in the surgical procedure. The early identification of problems has the potential to avoid many significant subsequent complications. The invention of the above-referenced application Ser. No. 12/842,606 involves a number of self tests which the thermal tissue operating system performs on itself, preferably upon initial start-up or powering-on of the system. These self tests are very useful for identifying a number of different, potential problems which manifest themselves before the thermal tissue operating system is used during a surgical procedure. However, many of the initial start-up or power-on tests are performed only once before commencing a surgical procedure. The surgical procedure could continue for many hours, during which other problems might arise from repeated use of the thermal tissue operating system during the course of the surgical procedure.

SUMMARY OF THE INVENTION

It is desirable to identify potential problems with a thermal tissue operating system that might develop as a result of ongoing use of the system during a surgical procedure. An early identification of any problem avoids subsequent surgical complications and reduces the trauma on the patient caused by prolonging the initial surgical procedure or by performing subsequent surgical procedure to correct an inadequate thermal tissue operation performed during the prior surgical procedure.

The present invention relates to a functional verification test which is performed on an ongoing basis, between thermal tissue operations conducted during the course of the entire surgical procedure, to detect potential problems in the performance of the thermal tissue operating system which might arise due to ongoing use during the course of its use in the procedure. Specifically, an ongoing functional verification test described herein recognizes the possibility of changes occurring in the jaw heating elements during the course of the procedure and that those changes may limit or inhibit the ability to perform reliable thermal tissue operations as intended. The functional verification test reduces the chances that a problem related to the jaw heating elements will go unnoticed during some part of the surgical procedure.

A relatively small amount of power from an energy source is applied to a jaw heating element during a test interval between individual thermal tissue operations. The test intervals are repeated throughout the surgical procedure. The electrical response characteristics of the jaw heating elements are measured and used to evaluate the integrity and functionality of the resistive heating elements of the jaws. In addition, the operational characteristics of the energy source of the thermal tissue operating system may also be evaluated to determine whether the energy source is functioning as expected.

In accordance with these and other considerations, this invention relates to a thermal tissue operating system for performing thermal tissue operations includes an energy source and a handpiece connected to the energy source. The handpiece includes a pair of opposing jaws which compress tissue during the thermal tissue operation. At least one of the jaws includes a jaw heating element for converting electrical power to thermal heat energy that is applied to the compressed tissue. The energy source supplies a heater power signal to the jaw heating element during the thermal tissue operation. The energy source further comprises a controller which controls the heater power signal supplied to the jaw heating element, a voltage sensor connected to the controller and operative to sense the voltage of the heater power signal supplied to the jaw heating element and to supply a voltage sense signal related to the sensed voltage of the heater power signal, a current sensor connected to the controller and operative to sense the current of the heater power signal supplied to the jaw heating element and to supply a current sense signal related to the sensed current of the heater power signal. The controller responds to the voltage sense signal and the current sense signal to calculate a resistance value of the jaw heating element, to compare the calculated resistance value to a predetermined range of expected resistance values of the heating element, and to signal an error state and to terminate delivery of the heater power signal to the jaw heating element upon the calculated resistance value falling outside of the predetermined range of expected resistance values.

In addition, this invention relates to a method of performing a functional verification test of a thermal tissue operating system which includes an energy source which produces electrical power and a handpiece which connects to the energy source. The handpiece includes a pair of opposing jaws which compress tissue during a thermal tissue operation. At least one of the jaws includes a jaw heating element for converting electrical power into thermal heat energy applied to the compressed tissue during the thermal tissue operation. The method comprises supplying a test heater power signal to the jaw heating element during test intervals when the energy source is not energizing the jaw heating element in a thermal tissue operation, sensing the current and the voltage of the test heater power signal, calculating a resistance value of the jaw heating element from the sensed current and voltage, referencing a range of expected resistance values of the jaw heating element which indicate normal characteristics of the jaw heating element, comparing the calculated resistance value with the range of expected resistance values, and communicating an error message when the calculated resistance value is outside of the range of expected resistance values.

Subsidiary features of the invention involve some or all of the following: supplying the test heater power signal at a lesser amount of power compared to the amount of power supplied in an operational heater power signal that is used to perform a thermal tissue operation; establishing each test interval to have the same time duration; creating a relatively greater duty cycle for the heater power signal during a thermal tissue operation and a relatively lesser duty cycle for the test heater power signal; calculating the resistance value of the jaw heating element from a peak voltage signal and a peak current signal created by the test heater power signal; and comparing the calculated resistance value to the predetermined range of expected resistance values during each test interval.

A more complete appreciation of the features of the present invention and its scope may be obtained from the accompanying drawings, which are briefly summarized below, from the following detailed description of a presently preferred embodiment of the invention, and from the appended claims.

BRIEF DESCRIPTION OF THE DRAWINGS

FIGS. 7A-7H are graphs of exemplary signals in the energy source shown in FIG. 6, all of which share a common time axis. Specifically for two sequential control cycles, FIGS. 7A and 7B show opposite phase square wave signals generated by an oscillator of one jaw energizing circuit of the energy source; FIG. 7C shows a relatively low duty cycle gate control signal supplied by a controller to an oscillator of one jaw energizing circuit of the energy source; FIG. 7D shows an input power signal to a transformer of the jaw energizing circuit, formed in response to the gate control signal shown in FIG. 7C; FIG. 7E shows a heater power signal created by the transformer of the jaw energizing circuit in response to the input power signal shown in FIG. 7D; FIG. 7F shows a relatively high duty cycle gate control signal supplied by the controller to an oscillator of one jaw energizing circuit of the energy source; FIG. 7G shows an input power signal to a transformer of the jaw energizing circuit, formed in response to the gate control signal shown in FIG. 7F; and FIG. 7H shows a heater power signal created by the transformer of the jaw energizing circuit in response to the input power signal shown in FIG. 7G.

FIGS. 8A-8C are graphs of signals exemplary of those present in the energy source and handpiece shown in FIG. 6, all of which share a common time axis. Specifically, FIG. 8A shows a waveform illustrative of either a voltage or current sense signal applied to a peak detector; FIG. 8B shows a reset signal supplied to the peak detector; and FIG. 8C shows a peak signal representative of the peak value which is detected and held by the peak detector in response to the sense signal shown in FIG. 8A, with the sense signal also shown in phantom in FIG. 8C.

FIG. 9 is a graph showing an exemplary characteristic relationship of temperature versus resistance of a jaw heating element of the handpiece shown in FIGS. 5 and 6.

DETAILED DESCRIPTION

Figure 1:
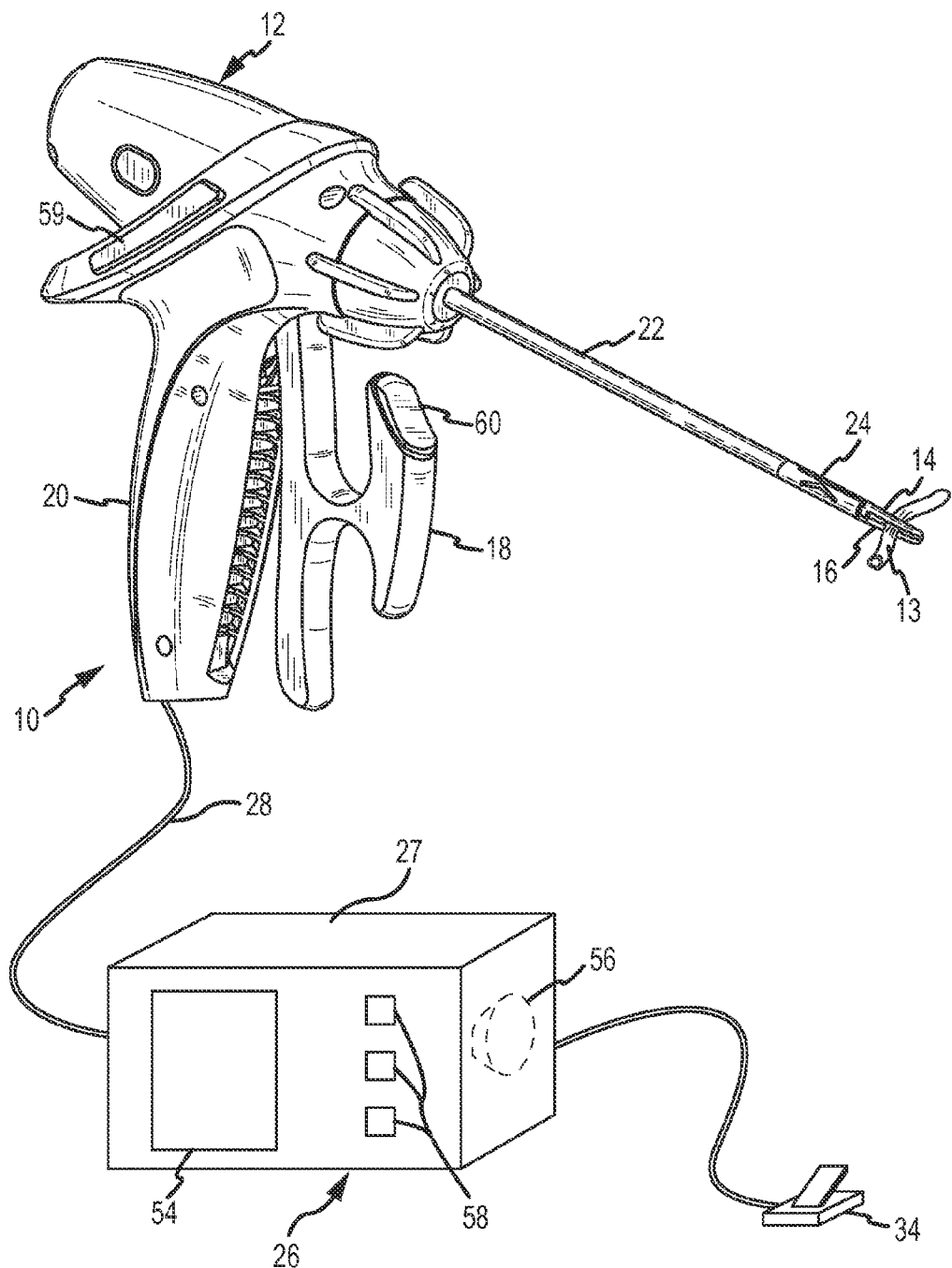
FIG. 1 is a perspective view of a handpiece and an energy source of a thermal tissue operating system which incorporates the present invention.

A thermal tissue operating system 10 in which the present invention is incorporated is shown in FIG. 1. The system 10 includes a handpiece 12 which is manipulated by a surgeon to grasp and compress tissue (exemplified by a vessel 13) between jaws 14 and 16 of the handpiece 12, and to simultaneously apply thermal heat energy from the jaws 14 and 16 to the compressed tissue in a thermal tissue operation. The thermal tissue operation may seal multiple pieces of the tissue together, cut a single piece of tissue into separate parts, or sequentially seal and then cut tissue.

The jaws 14 and 16 are brought together to compress the tissue by squeezing a lever 18 toward an adjacent handgrip 20 of the handpiece 12. Internal mechanical components of the handpiece 12 (not shown but described in the above-application Ser. No. 12/842,399 convert the pivoting movement of the lever 18 relative to the handgrip 20 into motion which is transferred through a shaft 22 to a jaw movement mechanism 24 (which is described in detail in the above application Ser. No. 12/842,327. The jaw movement mechanism 24 converts the longitudinal movement from the shaft 22 into movement to move the jaws 14 and 16 toward and away from one another. Movement of the jaws 14 and 16 toward one another grips and compresses the tissue between the jaws. Movement of the jaws 14 and 16 away from one another opens the jaws sufficiently to accept tissue between them before gripping and compressing the tissue and releases any tissue previously gripped.

The thermal tissue operating system 10 also includes an electrical energy source 26 which is connected by a cable 28 to the handpiece 12. The energy source 26 includes electrical components (FIGS. 5 and 6) housed within an enclosure 27. The energy source 26 supplies electrical power through the cable 28 to a pair of heat-producing resistive elements (30 and 32, FIGS. 5 and 6) that are embedded within or associated with the jaws 14 and 16 (FIG. 1). Electrical power conducted through the jaw heating elements (30 and 32, FIGS. 5 and 6) is converted into heat energy and is applied to the tissue gripped and compressed between the jaws 14 and 16 during the thermal tissue operation.

Electrical power is supplied when the lever 18 is pulled into proximity with the handgrip 20 and one of the switches 59 or 60 is pressed, thereby delivering a user activation signal from the handpiece 12 to the energy source 26. In response to the user activation signal, the energy source 26 delivers electrical power to the jaw heating elements (30 and 32, FIGS. 5 and 6) of the jaws 14 and 16. Alternatively, the activation signal may be supplied by pulling the lever 18 into proximity with the handgrip 20 and pressing a foot switch 34 which is connected to the energy source 26. The surgeon depresses the foot switch 34 with his or her foot.

To accomplish a thermal tissue operation, the energy source 26 delivers electrical power to the jaw heating elements (30 and 32, FIGS. 5 and 6), and that electrical power is converted into thermal energy and applied to the tissue. The thermal energy is delivered to the tissue compressed between the jaws 14 and 16 in accordance with a temperature versus time profile (36 or 36', 37, 46, FIG. 2A or 2B, 3 and 4) which is established for each type of thermal tissue operation. The temperature is achieved and controlled by the rate of energy delivered from the energy source 26 using temperature-based feedback signals from the jaws 14 and 16 of the handpiece 12. The energy source 26 controls the rate of electrical energy delivery to the jaw heating elements based on the measurement of the temperature at the jaws 14 and 16 for the duration of the thermal tissue operation. Desired temperature versus time profiles to accomplish the thermal tissue operations are shown in FIGS. 2A, 2B, 3 and 4.

Figure 2A:
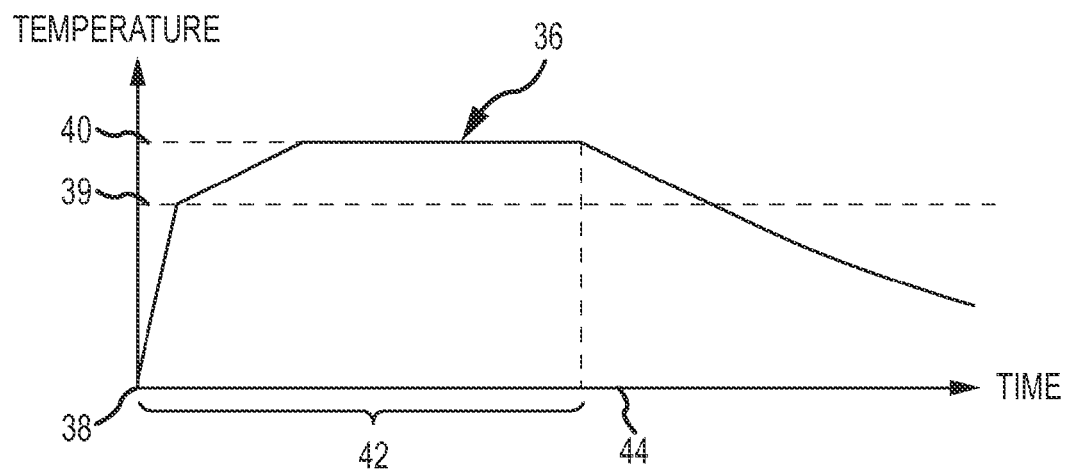
FIGS. 2A and 2B are graphs showing temperature versus time profiles for two different tissue sealing operations performed by the use of the thermal tissue operating system shown in FIG. 1.

One exemplary temperature versus time profile 36 for accomplishing a tissue sealing operation is shown in FIG. 2A. At time 38, the energy source 26 receives the activation signal to initiate the tissue sealing operation. The energy source 26 immediately delivers relatively high or maximum power to the jaw heating elements (30 and 32, FIGS. 5 and 6) to rapidly achieve a preliminary sealing temperature 39. Thereafter, the energy source 26 delivers a relatively lower amount of power to the jaw heating elements to achieve the final sealing temperature 40 less rapidly. Reducing the rate of temperature increase from the preliminary sealing temperature 39 to the final sealing temperature 40 reduces the possibility of an overshoot in the final sealing temperature 40. Upon reaching the final sealing temperature 40, the energy source 26 regulates the amount of electrical power supplied to the jaw heating elements to maintain the temperature 40 over the remaining portion of a tissue sealing time interval 42.

The length of tissue sealing time interval 42 ends when either a predetermined minimum amount of electrical energy has been transferred to the jaw heating elements and a predetermined minimum amount of time has elapsed from the activation time 38, or a predetermined maximum amount of time for the sealing time interval 42 has elapsed. The amount of electrical energy transmitted to the tissue is the sum of the electrical energy transmitted to both jaw heating elements (30 and 32, FIGS. 5 and 6) of the jaws 14 and 16 (FIG. 1). The total amount of electrical energy delivered throughout the progression of the time interval 42 is calculated and compared to the predetermined combined minimum amount of electrical energy, and the time elapsed since the start of the tissue sealing operation at 38 is compared with the predetermined minimum and maximum times for the tissue sealing operation to determine when either of the two above-described conditions for ending the tissue sealing operation are met.

When either of the two above-described conditions for ending the tissue seal operation are met, the energy source 26 terminates the delivery of power to the jaw heating elements, allowing the jaw heating elements to cool and decrease in temperature. The preferred sealing temperature 40 is approximately 170° C., and the predetermined minimum and maximum tissue sealing times vary from approximately 2 to 5 seconds, respectively. Preferably, the sealing temperature 40, the minimum and maximum tissue sealing times, and other information are stored within a handpiece processor 66 (FIGS. 5 and 6) of the handpiece 12 and are downloaded to the power system 26 prior to performing a thermal tissue operation. Different values of the thermal tissue operation-related variables are stored in different handpieces having different jaw heating elements with different electrical and thermal characteristics, to perform thermal tissue operations with the different types of handpieces.

Figure 2B:
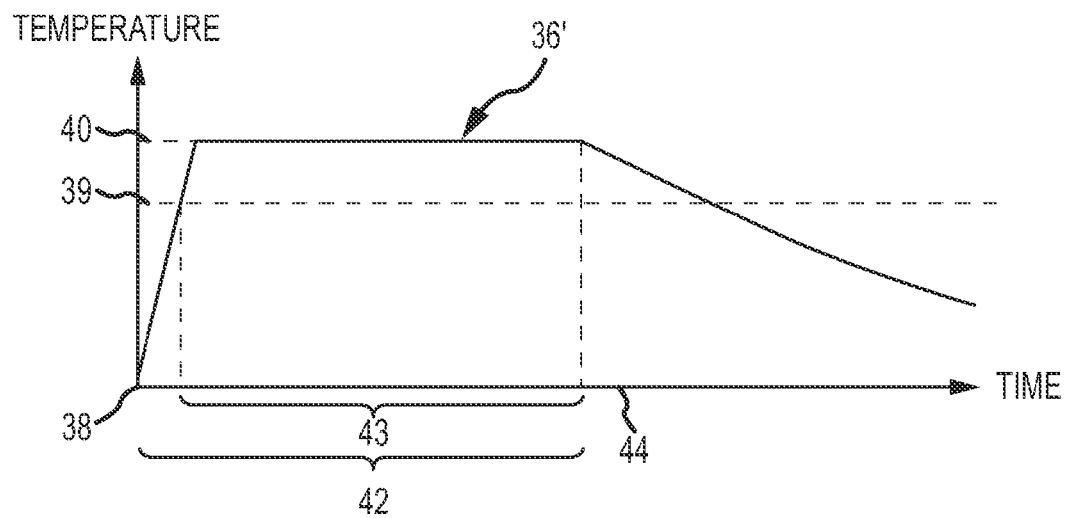

Another exemplary temperature versus time profile 36' for accomplishing a tissue sealing operation is shown in FIG. 2B. The temperature versus time profile 36' is similar to that profile 36 shown in FIG. 2A, except that the energy source 26 delivers relatively high or maximum power to the jaw heating elements (30 and 32, FIGS. 5 and 6) to achieve the final sealing temperature 40 more rapidly. Upon reaching the final sealing temperature 40, the energy source 26 regulates the amount of electrical power supplied to the jaw heating elements to maintain the temperature 40 during a final temperature maintenance time interval 43 after the final sealing temperature 40 is initially reached. The entire tissue sealing time interval 42 is therefore slightly greater in time than the final temperature maintenance interval 43, because the entire tissue sealing time interval 42 also includes the time between the assertion of the initial user activation signal at 38 until the final sealing temperature 40 is reached at the beginning of the final temperature maintenance interval 43.

In the tissue sealing temperature versus time profile 36', the final sealing temperature 40 is maintained for the duration of the maintenance time interval 43. The tissue sealing time interval 42 ends when the final sealing temperature 40 has been maintained within slight limits of variation for the duration maintenance time interval 43. No determination is made of whether a predetermined minimum amount of electrical energy has been transferred to the jaw heating elements when the tissue sealing profile 36' is performed. The time elapsed since the activation time 38 is measured, and if that time exceeds a predetermined maximum amount of time, the thermal tissue sealing operation is terminated because under the assumption that some issue has arisen which will prevent the proper execution of a sealing thermal tissue operation.

In the tissue sealing thermal operation represented by the temperature versus time profile 36', the final temperature maintenance interval 43 is approximately 2 seconds in time duration and the final sealing temperature 40 is approximately 150° C. Timing the 2 second final temperature maintenance interval 43 begins when the temperature is within approximately 10° C. of the desired 150° C. final sealing temperature 40. The temperature 39 exemplifies the starting point for measuring the temperature maintenance interval 43, because the temperature 39 is approximately 10° C. less than the final desired sealing temperature. The benefit of the tissue sealing profile 36' over the tissue sealing profile 36 (FIG. 2A) is that, in some cases involving some tissues in some procedures, adequate tissue seals may be obtained using a lower temperature for a shorter duration of time.

The predetermined maximum time duration allowable for a thermal tissue sealing operation, the final desired 150° C. temperature, and other information are stored within a handpiece processor 66 (FIGS. 5 and 6) of the handpiece 12 and are downloaded to the energy source 26 prior to performing a thermal tissue operation. Different values of the thermal tissue operation-related variables are stored in different handpieces having different jaw heating elements with different electrical and thermal characteristics, to perform thermal tissue operations with the different types of handpieces.

Figure 3:
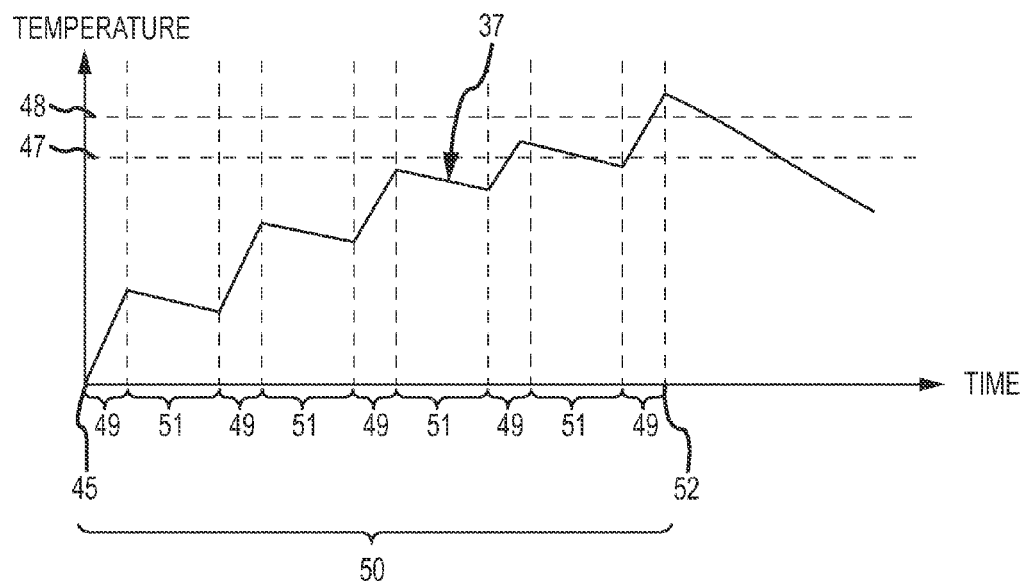
FIG. 3 is a graph showing a temperature versus time profile for a tissue cutting operation performed by the use of the thermal tissue operating system shown in FIG. 1.

A tissue cutting operation can also be performed independently of a tissue seal operation. A tissue cutting operation is typically performed after one or more tissue sealing operations have sealed the tissue or vessel which is to be cut. An exemplary temperature versus time profile 37 for accomplishing a tissue cut operation is shown in FIG. 3. At time 45, an activation signal is delivered to the energy source 26, and the tissue cutting operation starts. During the tissue cutting operation, the energy source 26 alternately supplies relatively high power to the jaw heating elements during power delivery periods 49 followed by terminating the supply of power to the jaw heating elements during power off periods 51. The power delivery periods 49 are preferably about 100 ms in time duration and the power off periods 51 are preferably about 200 ms in duration. The power delivery periods 49 and power off periods 51 are repeated in succession until the temperature of the jaw heating elements reaches a preliminary cutting temperature 47. Thereafter, a lower amount of power is delivered during the following power delivery periods 49. The power delivery periods 49 and power off periods 51 are continued until the temperature of the jaw heating elements reaches a final cutting temperature 48, at which time 52 the tissue cutting operation is complete and the supply of power to the jaw heating elements is terminated completely.

Preferred temperatures for the respective preliminary and final cutting temperatures 47 and 48 vary depending on the electrical and thermal characteristics of the jaw heating elements, but are generally between 200-240° C. and 270-280° C., respectively. A slight amount of overshoot of both the preliminary and final cutting temperatures 47 and 48 may occur during the respective power delivery periods 49 when the temperatures 47 and 48 are first reached. This slight overshoot is due to the energy source 26 completing the delivery of power during the power delivery period 49 when the temperatures 47 and 48 are first attained.

The time between the start time 45 and finish time 52 of the tissue cutting operation is the cutting time interval 50. The cutting time interval 50 varies for different tissue cutting operations due to differences in the amount of tissue to be cut between the jaws 14 and 16 (FIG. 1), the temperature of the jaw heating elements at the start time 45 of the cutting time interval 50, and the electrical and thermal characteristics of the jaw heating elements, among other factors.

The amount of energy delivered during the cutting time interval 50 is sufficient to disintegrate the tissue squeezed and compressed between the jaws 14 and 16 (FIG. 1). The disintegration permits the tissue to be separated into parts, without destroying, disintegrating or otherwise adversely compromising the quality of a seal which may be closely located on opposite sides of a generally linear delineation where the tissue cutting or disintegration occurs.

The successive power delivery periods 49 and power off periods 51 cause the temperature versus time profile 37 for the tissue cutting operation to resemble an inclined saw tooth shape. The inclined saw tooth shaped tissue cutting profile has been discovered to possess superior tissue cutting characteristics versus a conventional ramp profile when the temperature is continually increased until a desired final cutting temperature is reached.

Figure 4:
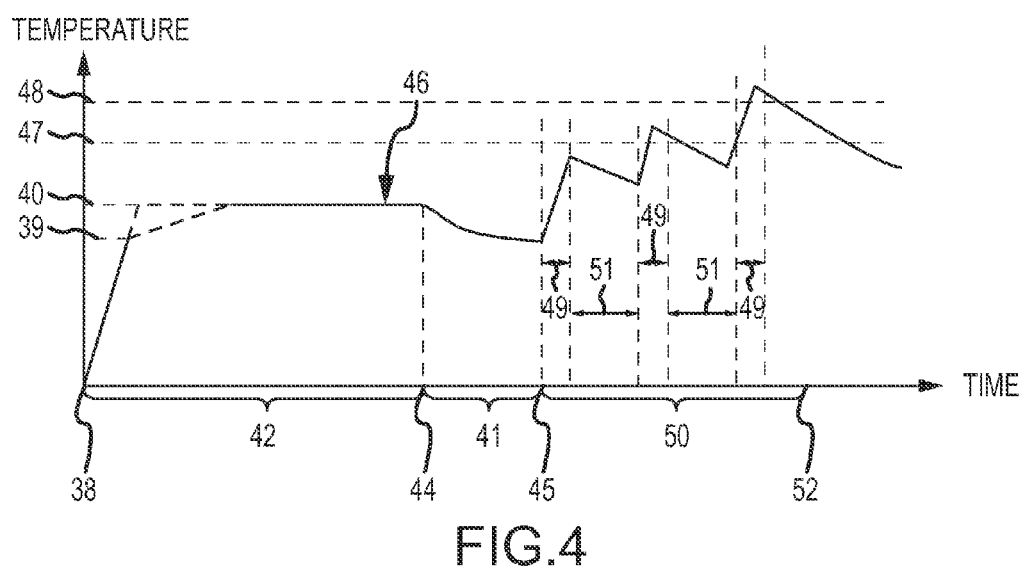
FIG. 4 is a graph showing a temperature versus time profile for a combined tissue sealing and cutting operation performed by use of the thermal tissue operating system shown in FIG. 1.

The temperature versus time profiles 36 (FIG. 2A) and 37 (FIG. 3) can be combined to form a temperature versus time profile 46, shown in FIG. 4, for a combined tissue sealing and cutting operation. The temperature versus time profiles 36' (FIG. 2B) and 37 (FIG. 3) can also be combined to form a temperature versus time profile (not specifically shown but similar to the profile 46 shown in FIG. 4) for a combined tissue sealing and cutting operation. The combined tissue sealing and cutting temperature versus time profile 46 resembles the temperature versus time profile 36 (FIG. 2A) or 36' (FIG. 2B) from a starting time 38 to an intermediate time 44 when the tissue sealing profile portion (36 or 36', FIG. 2A or 2B) of the operation is complete. The tissue is then allowed to cool slightly during a cooling time interval 41 between the end of the tissue sealing operation at time 44 and the start of the tissue cutting operation at time 45. The cooling time interval 41 is approximately one second in duration, and is instrumental in contributing to a more effective and efficient tissue sealing and cutting operation, compared to performing the tissue sealing and cutting operations directly in sequence without a cooling time interval 41.

Between times 45 and 52, the temperature versus time profile 46 resembles the temperature versus time profile 37 (FIG. 3) of the tissue cutting operation. The energy source 26 alternately supplies relatively high power to the jaw heating elements during power delivery periods 49 followed by terminating the supply of power to the jaw heating elements during power off periods 51. The power delivery periods 49 are preferably about 100 ms in time duration and the power off periods 51 are preferably about 200 ms in duration. The power delivery periods 49 and power off periods 51 are repeated in succession until the temperature of the jaw heating elements reaches a preliminary cutting temperature 47. Thereafter, a lower amount of power is delivered during the following power delivery periods 49. The power delivery periods 49 and power off periods 51 are continued until the temperature of the jaw heating elements reaches a final cutting temperature 48, at which time 52 the tissue cutting operation is complete and the supply of power to the jaw heating elements is terminated completely.

Preferred temperatures for the respective preliminary and final cutting temperatures 47 and 48 vary depending on the electrical and thermal characteristics of the jaw heating elements, but are generally between 200-240° C. and 270-280° C., respectively. A slight amount of overshoot of both the preliminary and final cutting temperatures 47 and 48 may occur during the respective power delivery periods 49 when the temperatures 47 and 48 are first reached. This slight overshoot is due to the energy source 26 completing the delivery of power during the power delivery period 49 when the temperatures 47 and 48 are first attained.

The time between the start time 45 and the finish time 52 of the tissue cutting operation is the cutting time interval 50. The cutting time interval 50 varies for different tissue cutting operations due to differences in the amount of tissue to be cut between the jaws 14 and 16 (FIG. 1), the temperature of the jaw heating elements at the start time 45 of the cutting time interval 50, and the electrical and thermal characteristics of the jaw heating elements, among other factors.

As shown in FIG. 1, a display 54 and a speaker 56 are included within the enclosure 27 of the energy source 26. The display 54 and the speaker 56 convey information about the functional response characteristics of the thermal tissue operating system 10, during use of the system. The energy source 26 also includes mode selection controls or switches 58. The handpiece 12 includes selection thumb switches 59 on opposite sides of the handgrip 20 (only one selection switch 59 is shown in FIG. 1). The handpiece 12 also includes a finger selection switch 60 on the lever 18. The mode control switches 58 are used to select between a manual mode of operation and an automatic mode of operation. In the manual mode of operation, a tissue cut operation is activated by pulling the lever 18 back toward the handgrip 20 and then depressing one of the thumb switches 59. In the manual mode of operation, a tissue seal operation is activated by depressing the finger switch 60 when the lever 18 is pulled back toward the handgrip 20. In the automatic mode of operation, a combined tissue sealing and cutting operation is activated by depressing the switch 60 when the lever 18 is pulled back toward the handgrip 20. In the automatic mode of operation, pressing the switch 59 with the lever 18 pulled back toward the handgrip 20 activates a manual cut operation.

The present invention relates to performing a functional verification test at test intervals which occur between sequential thermal tissue operations during the course of the surgical procedure. The functional verification test is principally useful to determine whether potentially-degrading changes have occurred in the resistance characteristics of the jaw heating elements 30 and 32 of the handpiece 12. The functional verification test is also useful to determine other aspects of proper operation of the energy source 26. The details of the functional verification test are described below in connection with FIG. 10. The details of the functional verification test are understood by reference to FIGS. 5-9.

Figure 5:
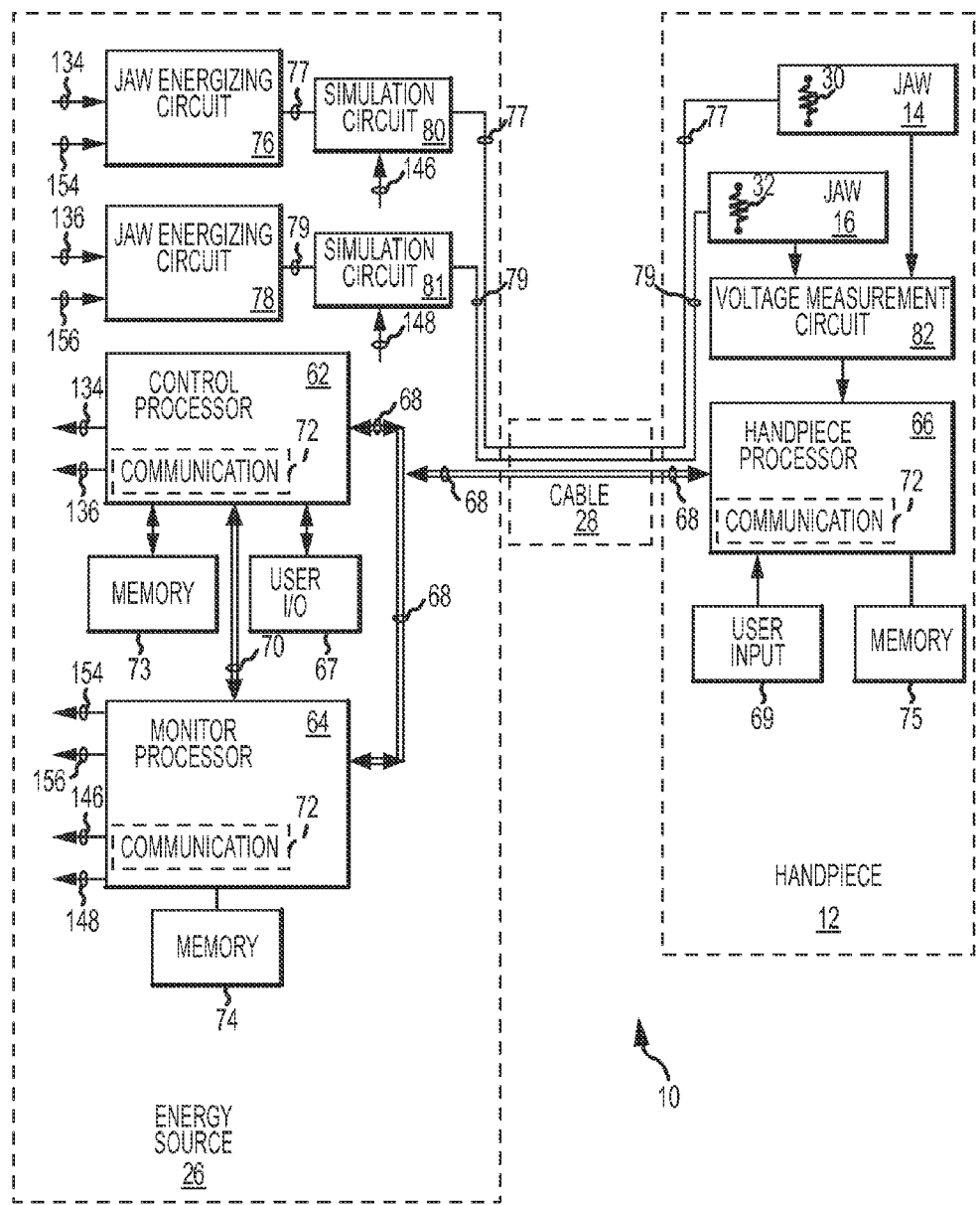
FIG. 5 is a block diagram of certain electrical components of the energy source and the handpiece shown in FIG. 1.

As shown in FIG. 5, the energy source 26 includes a control processor 62 and a monitor processor 64. The control processor 62 generally controls the operation and overall functionality of the energy source 26, as well as performing and participating in the performance of the self-tests described herein. The monitor processor 64 monitors the operation of the control processor 62 and otherwise performs many of its own functional tests to ensure that the control processor 62 and other sub-components are operating as expected.

A handpiece processor 66 of the handpiece 12 controls the operation of the handpiece 12, in response to signals from the lever 18 and switches 59 and 60 (FIG. 1) and signals from the control processor 62 communicated over a communication bus 68 which is part of the cable 28 (FIG. 1) connecting the energy source 26 with the handpiece 12. The monitor processor 64 is also connected to the communication bus 68 to enable it to communicate with the handpiece processor 66 and the control processor 62. In addition, the control processor 62 and the monitor processor 64 are directly connected together by a separate bus 70, for direct communication of signals between those processors 62 and 64.

Either individually or by cooperative combination of functionalities with one or more of the other processors, one or more of the processors 62, 64 and 66 constitute a controller for the energy source 26, a controller for the handpiece 12, and a controller for the thermal tissue operating system 10. Even though the components 62, 64 and 66 are described in their exemplary form as processors, any type of computational device, data processing device, controller or programmable logic gate device, which is capable of performing the functions described herein as attributable to the components 62, 64 and 66, may constitute processors 62, 64 and 66.

Communication between the processors 62, 64 and 66 is accomplished by using a predefined communication protocol, which is implemented within a communication routine 72 of the control processor 62, the monitor processor 64 and the handpiece processor 66. Executing the communication routine 72 allows the transfer of information between the processors 62, 64 and 66 over the bus 68. The processors 62, 64 and 66 include memory modules 73, 74 and 75, which store the programs that the processors 62, 64 and 66 execute to achieve their respective functionalities. In addition, user input and output (I/O) 67 is communicated to the control processor 62 by use of the display 54, the speaker 56 and the front panel controls 58 of the energy source (FIG. 1). User input 69 is also communicated to the handpiece processor 66 by movement of the lever 18 and the depression of the thumb switches 59 and finger switch 60 (FIG. 1).

The energy source 26 also includes a first jaw energizing circuit 76 which supplies a heater power signal 77 to the heating element 30 in the jaw 14 of the handpiece 12. The energy source 26 also includes a second jaw energizing circuit 78 which supplies a heater power signal 79 to the heating element 32 in the jaw 16 of the handpiece 12. The heater power signals 77 and 79 establish the amount of electrical power delivered to the jaw heating elements 30 and 32. The heater power signals 77 and 79 are converted into thermal energy by the jaw heating elements 30 and 32 to accomplish the thermal tissue operations. The heater power signals 77 and 79 are conducted from the energy source 26 to the handpiece 12 through conductors in the cable 28.

The jaw energizing circuits 76 and 78 are independently and respectively controlled by the control processor 62 asserting gate control signals 134 and 136. The gate control signals 134 and 136 control characteristics of the separate heater power signals 77 and 79 delivered to each jaw heating element 30 and 32, thereby allowing the temperature of each jaw heating element 30 and 32 to be individually controlled in response to individual temperature feedback controls from each jaw heating element. Independent regulation of the temperature of each heating element 30 and 32 allows the temperature of the tissue gripped between the jaws 14 and 16 to be more precisely controlled to achieve the desired temperature characteristics for a seal operation, a cut operation and a combined seal and cut operation. The monitor processor 64 enables the jaw energizing circuits 76 and 78 to deliver the heater power signals 77 and 79 by asserting enable signals 154 and 156, respectively. Whenever an enable signal 154 or 156 is de-asserted, the respective jaw energizing circuit 76 or 78 will not create the heater power signal 77 or 79.

Simulation circuits 80 and 81 are connected to the jaw energizing circuits 76 and 78 to receive the heater power signals 77 and 79, respectively, under the control of the monitor processor 64, when it is desired to conduct certain functional integrity tests described below. When deactivated by the monitor processor 64 de-asserting activation signals 146 and 148, the simulation circuits 80 and 81 conduct the heater power signals 77 and 79 through internal load simulating heating elements (150 and 152, FIG. 6) within the simulation circuits 80 and 81, respectively. When activated by the monitor processor 64 asserting the activation signals 146 and 148, the simulation circuits 80 and 81 conduct the heater power signals 77 and 79 to the heating elements 30 and 32 of the jaws 14 and 16, respectively. Conducting the functional integrity tests of the energy source 26 with the simulation circuits 80 and 81 ensures that the thermal tissue operating system is working properly.

The handpiece 12 includes a voltage measurement circuit 82 that detects the voltage across the heating elements 30 and 32 of the jaws 14 and 16 when the heater power signals 77 and 79 cause current flow through those heating elements 30 and 32. The handpiece processor 66 communicates the voltage values from the measurement circuit 82 over the bus 68 to the control and monitor processors 62 and 64. The control processor 62 uses those voltage values to calculate power and energy delivered to and consumed by the heating elements 30 and 32. Measuring the voltage across the heating elements 30 and 32 at the jaws provides greater accuracy in the measurement of the power and energy consumed by the jaw heating elements 30 and 32, because losses resulting from conducting the power heating signals 77 and 79 through the conductors of the cable 28 are not involved in the voltage values detected by the measurement circuit 82. Independent determinations of the power and energy delivered to and consumed by each of the heating elements 30 and 32 facilitate individual control over each of the heating elements 30 and 32.

More details concerning the jaw energizing circuits and 76 and 78, the simulation circuits 80 and 81 and the functionality of the control and monitor processors 62 and 64 of the energy source 26, as well as the heating elements 30 and 32, the measurement circuit 82 and the handpiece processor 66 of the handpiece 12, are shown and discussed in connection with FIG. 6.

The jaw energizing circuits 76 and 78 are each substantially identical in construction and functionality, although each jaw energizing circuit 76 and 78 is separately controllable. Each jaw energizing circuit 76 and 78 respectively includes a variable voltage power supply 84 and 86. Each variable voltage power supply 84 and 86 is connected to a conventional commercial energy source (not shown). Each power supply 84 and 86 converts commercial power to direct current power at a voltage established by each power supply 84 and 86 in response to voltage control signals 88 and 90 supplied by the control processor 62 to each power supply 84 and 86, respectively. Each jaw energizing circuit 76 and 78 is therefore capable of supplying the heater power signal 77 and 79, respectively, at different and individually controlled voltage levels established by the control signals 88 and 90.

Voltage sensors 92 and 94 are connected to sense the output voltage from the variable voltage power supplies 84 and 86. The voltage sensors 92 and 94 supply voltage sense signals 96 and 98 to the monitor processor 64 in response to the voltages of the electrical energy delivered from the variable voltage power supplies 84 and 86. The ability to individually adjust the voltage from each power supply 84 and 86 allows adjustment to compensate for slight variations in the resistances of each jaw heating element 30 and 32. Changing the voltage to compensate for a slightly changed resistance of a jaw heating element 30 or 32 causes each jaw heating element to consume approximately the same amount of electrical energy and thereby generate approximately the same amount of thermal energy, for similar gate control signals applied, as discussed below.

Electrical energy at the output voltage of the power supplies 84 and 86 is supplied to center taps 100 and 102 of a center tapped primary winding of power output transformers 104 and 106, respectively. The primary windings of the power output transformers 104 and 106 are therefore divided into two winding segments 108, 110 and 112, 114 by the center taps 100 and 102, respectively. The upper (as shown) winding segments 108 and 112 are connected to switches 116 and 120, respectively. The lower (as shown) winding segments 110 and 114 are connected to switches 118 and 122, respectively. When the switches 116 and 120 are conductive, current is conducted through the winding segments 108 and 112 from the variable voltage power supplies 84 and 86 through current sensors 95 and 97, respectively, to reference potential 99. When the switches 118 and 122 are conductive, current is conducted through the winding segments 110 and 114 from the variable voltage power supplies 84 and 86, through the current sensors 95 and 97, respectively, to the reference potential 99.

Each of the jaw energizing circuits 76 and 78 includes its own oscillator 128 and 129, respectively. The switches 116 and 118 conduct in response to signals generated by the oscillator 128, and the switches 120 and 122 conduct in response to signals generated by the oscillator 129. The oscillators 128 and 129 each generate two substantially similar or identical relatively high frequency, e.g. 50 kHz, square wave signals 130 and 132 (FIGS. 7A and 7B). The square wave signals 130 and 132 are phase shifted with respect to one another by 180 degrees. The square wave signal 130 is applied to the switches 116 and 120. The square wave signal 132 is applied to the switches 118 and 122. The switches 116-122 are capable of conducting current from the primary winding segments 108-114 of the of the power output transformers 104 and 106, only when the square wave signals 130 and 132 are a positive value. During the times that the square wave signals 130 and 132 are at reference or zero value, the switches 116-122 are not capable of conducting.

A gate control signal 134 is applied from the control processor 62 to the oscillator 128, and a gate control signal 136 is applied from the control processor 62 to the oscillator 129. Upon assertion of the gate control signal 134, the oscillator 128 conducts the square wave signals 130 and 132, respectively, for the duration of the assertion of the gate control signal 134. Because the square wave signals 130 and 132 are phase shifted with respect to one another by 180 degrees, the alternating conductivity of the switches 116 and 118 conducts current in opposite directions through the primary windings 108 and 110 from the center tap 100, thereby establishing a primary alternating current signal 138 (FIG. 7D) which is conducted through the primary winding segments 108 and 110 of the power output transformer 104. Similarly, upon assertion of the gate control signal 136, the oscillator 129 conducts the square wave signals 130 and 132, respectively, for the duration of the assertion of the gate control signal 136. Because the square wave signals 130 and 132 are phase shifted with respect to one another by 180 degrees, the alternating conductivity of the switches 120 and 122 conducts current in opposite directions through the primary windings 112 and 114 from the center tap 102, thereby establishing a primary alternating current signal 140 (FIG. 7G) which is conducted through the primary winding segments 112 and 114 of the power output transformer 106. The primary alternating current signals 138 and 140 induce the heater power signals 77 and 79 from the secondary windings 124 and 126 of the power output transformers 104 and 106, respectively.

The amount of electrical energy contained in the heater power signals 77 and 79 is directly related to the voltage from the variable voltage power supplies 84 and 86, respectively, and is also directly related to the time duration of the gate control signals 134 and 136. Asserting the gate control signals 134 and 136 for a longer time duration results in the switches 116, 118 and 120, 122 conducting the primary alternating current signals 138 and 140 through the primary winding segments 108, 110 and 112, 114 of the power output transformers 104 and 106 for a greater duration of time, thereby causing greater energy content in the heater power signals 77 and 79, respectively. Conversely, asserting the gate control signals 134 and 136 for a shorter time duration results in the switches 116, 118 and 120, 122 conducting the primary alternating current signals 138 and 140 through the primary winding segments 108, 110 and 112, 114 of the power output transformers 104 and 106 for lesser duration of time, thereby causing lesser energy in the heater power control signals 77 and 79.

The control processor 62 independently controls the duration of the gate control signals 134 and 136, thereby controlling the amount of electrical energy delivered to the jaw heating elements 30 and 32 for conversion into thermal energy to establish and maintain the desired temperature of the jaw heating elements. The thermal loads experienced by each of the jaws 14 and 16 are somewhat different. It is because of the different thermal loads that the control processor 62 exercises independent control over each of the jaw energizing circuits 76 and 78 by separately establishing the time duration of each of the gate control signals 134 and 136, which in turn separately establish the electrical energy content of the heater power signals 77 and 79. FIGS. 7C and 7F illustrate the separate and individual control of each gate control signal 134 and 136.

The power and consequently temperature control of the jaw heating elements 30 and 32 is performed by the control processor 62 on a control cycle basis. A control routine 103 is executed by the control processor 62 in accordance with the selected thermal tissue operation, and the temperature versus time profile 36 or 36', 37 and 46 (FIG. 2A or 2B, 3 and 4, respectively) of the selected thermal tissue operation, in response to the user activation signal. The control routine 103 invokes a conventional feedback pulse width modulation routine 101 that establishes the time duration of the gate control signals 134 and 136 for each control cycle 104 in relation to the temperature of the jaw heating elements 30 and 32. The control processor 62 supplies the gate control signals 134 and 136 to the oscillators 128 and 129, and the duration of the gate control signals 134 and 136 establish the desired number of pulses of the square wave signals 130 and 132 conducted during each control cycle to create heater power signals 77 and 79.

The duty cycle of the gate control signals 134 and 136 during each control cycle 104 controls the amount of electrical energy delivered to the jaw heating elements during that control cycle, as understood by reference to FIGS. 7A-7H. The exemplary signals shown in FIGS. 7A-7H extend over two control cycles 104. The square wave signals 130 and 132 produced by the oscillators 128 and 129 are shown in FIGS. 7A and 7B. A relatively low duty cycle gate control signal 134 supplied by the control processor 62 is shown in FIG. 7C. The relatively low duty cycle gate control signal 134 shown in FIG. 7C has an on time that extends from $t_0$ to $t_1$ and an off time that extends from $t_1$ to $t_3$ in the first shown control cycle 104 and an on time that extends from $t_3$ to $t_4$ and an off time that extends from $t_4$ to $t_6$ in the second control cycle 104. The relatively low duty cycle of the gate control signal 134 creates the primary alternating current signal 138 shown in FIG. 7D that is formed by two cycles of square wave signals 130 and 132.

A relatively high duty cycle gate control signal 136 supplied by the control processor 62 is shown in FIG. 7F. The relatively high duty cycle gate control signal 136 shown in FIG. 7F has a much longer on time and a much shorter off time compared to the on and off times of the gate control signal 134 shown in FIG. 7C. The on time of the relatively high duty cycle gate control signal 136 shown in FIG. 7F extends from $t_0$ to $t_2$ and its off time extends from $t_2$ to $t_3$ in the first control cycle 104. Similarly in the second control cycle 104 shown in FIG. 7F, the longer on time extends from $t_3$ to $t_5$ and the shorter off time extends from $t_5$ to $t_6$. The relatively high duty cycle of the gate control signal 136 creates the primary alternating current signal 140 shown in FIG. 7G that is formed by four cycles of square wave signals 130 and 132.

Thus, the control processor 62 varies the amount of energy of the heater power signals 77 and 79 by varying the duty cycle of the gate control signals 134 and 136. Varying the duty cycle of the gate control signals 134 causes the oscillators 128 and 129 to vary the number of pulses of the square wave signals 130 and 132 conducted to the switches 116-122, which in turn varies the time duration that the primary alternating current signals 138 and 140 are present during each control cycle 104. Fewer and greater numbers of pulses of the square wave signals 130 and 132 during each control cycle 104 result in less and more electrical energy reaching the jaw heating elements 30 and 32 during each control cycle 104, respectively. The exemplary control cycles shown in FIGS. 7A-7H have six pulses of square wave signals 130 and 132 forming each control cycle 104, for illustrative purposes only; in actuality, each control cycle 104 will typically have a considerably greater number of pulses of the square wave signals 130 and 132. In a practical embodiment of the thermal tissue operating system, the length of a control cycle 104 is about 5 ms.

Figure 6:
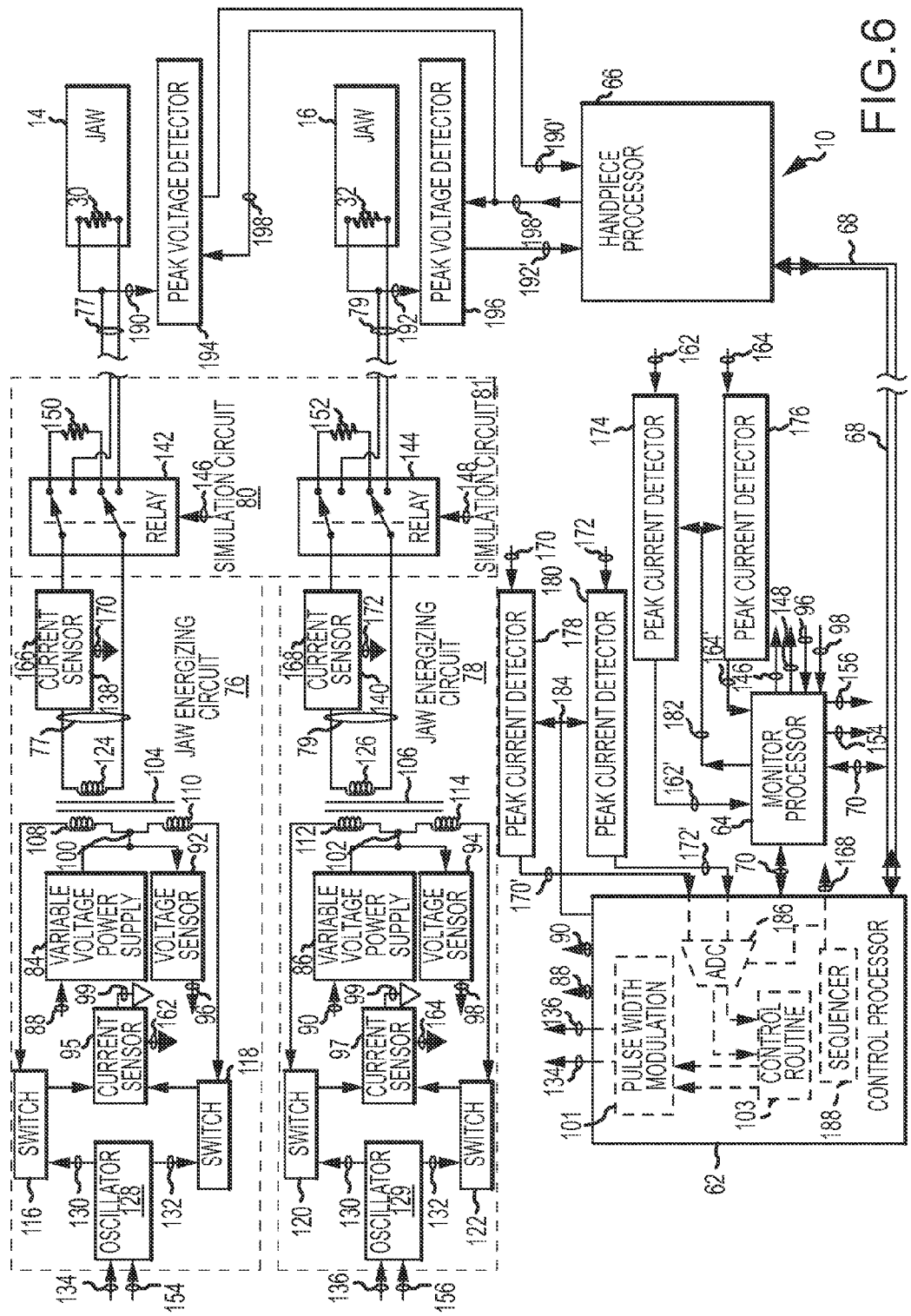
FIG. 6 is a more detailed block and schematic diagram of the energy source and handpiece shown in FIG. 5.

The primary alternating current signals 138 and 140 are conducted through the primary winding segments 108, 110 and 112, 114 of output transformers 104 and 106, as shown in FIG. 6. In response, the transformers 104 and 106 respectively induce heater power signals 77 and 79 from their secondary windings 124 and 126. Other than slight reductions caused by the losses which occur in the transformers 104 and 106, the energy content of the heater power signals 77 and 79 is approximately the same as the energy content of the primary alternating current signals 138 and 140.

The heater power signals 77 and 79 are conducted to relays 142 and 144 of the simulation circuits 80 and 81, respectively. The relays 142 and 144 are activated and deactivated by the assertion and deassertion of relay activation signals 146 and 148 supplied by the monitor processor 64. When the relays 142 and 144 are deactivated, the heater power signal 77 and 79 pass through the relays 142 and 144 to load-simulation heating elements 150 and 152. The load-simulation heating elements 150 and 152 are a part of the energy source 26 and are located within the enclosure 27 (FIG. 1) of the energy source 26. When the relays 142 and 144 are activated, the heater power signals 77 and 79 are conducted through the cable 28 to the jaw heating elements 30 and 32 of the handpiece 12.

For the heater power signals 77 and 79 to reach the jaw heating elements 30 and 32 of the handpiece 12, the monitor processor 64 must be fully functional and must determine that the operation of the energy source 26 and handpiece 12 is appropriate and within safe limits. It is under these circumstances that the relay activation signals 146 and 148 are asserted by the monitor processor 64, to activate the relays 142 and 144 and thereby permit the heater power signals 77 and 79 to reach the jaw heating elements 30 and 32, respectively. The relays 142 and 144 are examples of controllable switches that receive control signals, such as the relay activation signals 146 and 148, to change between conductive states.

In addition to deactivating the relays 142 and 144 to terminate the supply of power to the jaw heating elements 30 and 32, the monitor processor 64 can separately terminate the creation of the heater power signals 77 and 79 in the jaw energizing circuits 76 and 78, by deasserting enable signals 154 and 156 applied to the oscillators 128 and 129, respectively. The oscillators 128 and 129 generate the square wave signals 130 and 132 only when the enable signals 154 and 156 are asserted by the monitor processor 64. When the enable signals 154 and 156 are de-asserted, the oscillators 128 and 129 do not generate the square wave signals 130 and 132, and the heater power signals 77 and 79 are not created.

When the switches 116, 118 and 120, 122 are conductive, the current flowing through those switches passes through current sensors 95 and 97. The current sensors 95 and 97 measure the amount of current flowing through the primary winding segments 108, 110 and 112, 114 of the power output transformers 104 and 106, respectively. The sensors 95 and 97 supply primary winding current sense signals 162 and 164 having magnitudes which represent the magnitudes of the current flowing in the primary windings of the transformers 104 and 106, respectively. The voltage sensors 92 and 94 supply the voltage sense signals 96 and 98 which have magnitudes that represent the respective magnitudes of the voltage applied across the primary winding segments 108, 110 and 112, 114 of the transformers 104 and 106, respectively.

Current sensors 166 and 168 are connected to the secondary windings 124 and 126 of the power output transformers 104 and 106 to measure the current of the heater power signals 77 and 79, respectively. The current sensors 166 and 168 supply secondary or output current sense signals 170 and 172 having magnitudes which represent the magnitudes of the current of the heater power signals 77 and 79.

The primary current sense signals 162 and 164 are applied to peak current detectors 174 and 176, respectively, and the secondary current sense signals 170 and 172 are applied to peak current detectors 178 and 180, respectively. The peak current detectors 174-180 are each conventional and include conventional peak hold circuitry to detect and hold the highest or peak magnitude of any signal applied to the peak hold circuits, until the peak current detectors are reset. The peak current detectors 174, 176, 178 and 180 hold the peak magnitudes of the current signals 162, 164, 170 and 172, respectively, as peak magnitude current signals 162', 164', 170' and 172', until reset. The peak magnitude current signals 162', 164', 170' and 172' therefore represent the peak magnitudes of the current sense signals 162, 164, 170 and 172 during a sampling period of the detectors 174-180, respectively.

The sampling periods of the peak current detectors 174-180 are established by reset signals 182 and 184 which are asserted by the monitor and control processors 64 and 62 respectively. The reset signal 182 is asserted to the peak current detectors 174 and 176, and the reset signal 184 is asserted to the peak current detectors 178 and 180. The reset signals 182 and 184 (comparable to the reset signals 198a and 198b, FIG. 8B) are asserted once during each control cycle period 104 (FIGS. 7A-7H), to assure that the peak current values 162', 164', 170' and 172' of the current conducted during that control cycle are obtained for use by the control and monitor processors 62 and 64 in regulating the output power and in controlling and monitoring the functionality of the energy source 26.

The peak magnitude current signals 170' and 172' are supplied to an analog to digital converter (ADC) 186. As shown in FIG. 6, the ADC 186 is an internal component of the control processor 62; however, the ADC 186 could also be a separate external component of the control processor 62. The ADC 186 converts the analog values of the peak current signals 170' and 172' to corresponding digital values at sampling points within each control cycle period 104. The sampling points are determined by a sequencer 188, which generally controls the sequence of all functions performed by the control processor 62, including supplying the converted peak digital values 170' and 172' of the corresponding analog peak current signals 170 and 172 to other routines executed by the control processor 62. The monitor processor 64 and the handpiece processor 66 also have ADCs and sequencers (neither shown) which operate in a similar manner to the ADC 186 and the sequencer 188 of the control processor 62.

Voltage sense signals 190 and 192 represent the voltages across the jaw heating elements 30 and 32, respectively. The voltage sense signals 190 and 192 are supplied to peak voltage detectors 194 and 196 within the handpiece 12. The peak voltage detectors 194 and 196 are conventional and include circuitry which detects and holds the maximum or peak value of the voltage sense signals 190 and 192 until the peak voltage detectors 194 and 196 are reset. The detectors 194 and 196 supply peak voltage signals 190' and 192' to the handpiece processor 66. The peak voltage signals 190' and 192' correspond to the peak or maximum values of the analog voltage sense signals 190 and 192 over a sampling period of the peak voltage detectors 194 and 196. The sampling period of the peak voltage detectors 194 and 196 is established by a reset signal 198 (198a, 198b, FIG. 8B) asserted by the handpiece processor 66. The reset signal 198 is asserted once during each control cycle 104 (FIGS. 7A-7H), to assure that the peak values of the voltages applied to the jaw heating elements 30 and 32 during that control cycle are obtained for use in controlling and monitoring the functionality of the energy source 26.

The peak detectors 174, 176, 178, 180, 194 and 196 all operate in similar manner. The following description of peak detector functionality is presented in reference to exemplary signals shown in FIGS. 8A-8C applied to the peak voltage detector 196. The voltage sense signal 192 is shown in FIG. 8A as having a variable magnitude over two control cycles 104a and 104b. Each voltage sense signal 192 is formed by four positive half-cycles of the heater power signal 79 and four negative half-cycles of the heater power signal 79 (FIG. 7H). The positive and negative pulses of the heater power signal are rectified into positive values as shown in FIG. 8A by a conventional rectifying capability of the peak detector 196. The rectifying capability assures that the maximum value of both the positive and negative half-cycles of the heater power signal 79 are detected and held. The first cycle period 104a starts at time $t_0$ and ends at time $t_3$. The second cycle period 104b starts at time $t_3$ and ends at time $t_6$. Reset signals 198a and 198b are shown in FIG. 8B as asserted prior to times $t_3$ and $t_6$, prior to the start of both control cycles 104a and 104b. The assertion of the reset signals 198a and 198b cause the peak values 192' which are being held to dissipate or discharge as shown 199.

The peak voltage signal 192', shown in FIG. 8C, begins at a value which relates to the magnitude of the voltage sense signal 192 immediately after the reset signal has been de-asserted to the peak voltage detector 196. Sampling the peak voltage signal 192' begins at the start of the control cycle 104a and the maximum sampled magnitude for the duration of the first cycle period 104a is held until the reset signal 198a is asserted. The magnitude of the voltage sense signal 192 was near its maximum at the beginning of the control cycle 104a, as shown in FIG. 8C. When the reset signal 198a is de-asserted at time $t_3$ at the beginning of the second control cycle 104b, the magnitude of the voltage sense signal 192 has decreased compared to the magnitude of the voltage sense signal 192 shortly after time $t_0$. Consequently, the initial value of the peak voltage signal 192' at the beginning of the control cycle 104b starts low, but the magnitude of the peak voltage sense signal 192' continues to increase during the control cycle 104b, until heater power signal 79 (FIG. 7H) is no longer delivered when the gate control signal 136 is no longer asserted (FIGS. 6 and 7F). Thus, the continually increasing value of the peak voltage signal 192' during the cycle period 104b illustrates that each peak detector will increase the magnitude of its peak output signal whenever its input signal increases above a previous value, until reset.

The control processor 62 uses the peak voltage values 190' and 192' along with the peak current values 170' and 172' to individually calculate resistance values of the jaw heating elements 30 and 32 during each control cycle period 104. The control processor 62 obtains the peak current values 170' and 172' by sampling the peak current detectors 178 and 180 during each control cycle period 104. The control processor 62 obtains the voltage values across the heating elements 30 and 32 by issuing commands to the handpiece processor 66 requesting the peak voltage values 190' and 192' derived by the peak voltage detectors 194 and 196.

The control processor 62 calculates the resistance of each of the jaw heating elements 30 and 32 during each control cycle 104 by dividing the peak voltage values 190' and 192' for each jaw heating element 30 and 32 by the peak current values 170' and 172', respectively. The calculated resistance value is thereafter used to determine the temperature of each jaw heating element. The correlation between resistance value and temperature of each jaw heating element is obtained from the known temperature coefficient characteristic relationship between temperature and resistance of the material which forms each jaw heating element 30 and 32. Graph 200, shown in FIG. 9, illustrates an exemplary positive temperature coefficient and resistance relationship. The graph 200 illustrates that for each resistance of each jaw heating element, that heating element is experiencing a single temperature. By knowing the resistance, obtained from dividing the peak voltage value by the peak current value, the corresponding temperature of the jaw heating element is obtained.

The graph 200 can be defined by an equation or by a lookup table. In either case, the equation or lookup table is stored in the memory 75 of the handpiece 12 (FIG. 5). A separate equation or lookup tables stored in the handpiece memory 75 allows the data to be calibrated to the exact characteristic relationship of temperature and resistance of each jaw heating element 30 and 32 specifically used in each handpiece 12. The equation or the data from the lookup table in the memory 75 of the handpiece is sent to the control processor 62 over the communication bus 68 by the handpiece processor 66 when the handpiece 12 is initially connected to the energy source 26. In this manner, the temperature determinations are specific to the individual resistance characteristics of each jaw heating element 30 and 32.

The ability to control the level of voltage from each variable voltage power supply 84 and 86 allows that voltage to be increased or decreased to compensate for manufacturing variances and slight variations in resistance of the jaw heating elements 30 and 32. In the event that one of the jaw heating elements 30 or 32 has a higher or lower resistance value than expected, the voltage from the power supply 80 is increased or decreased to ensure the same power is simultaneously delivered to each jaw heating element 30 and 32. Prior to performing a thermal tissue operation, and periodically during the procedure, the control processor 62 calculates resistance values for the jaw heating elements 30 and 32 and then signals the variable voltage power supplies 84 and 86 to adjust the voltage supplied, so that an equivalent and desired amount of power is delivered to each jaw heating element.

The level of voltage supplied from the variable voltage power supplies 84 and 86 to each jaw heating element 30 and 32 is calculated as the square root of the product of the desired power consumption of the jaw heating element at a particular time in one of the temperature versus time profiles 36 or 36' (FIG. 2A or 2B), 37 (FIG. 3) or 46 (FIG. 4) and the calculated resistance value of that jaw heater. Varying the voltage supplied to the jaw heating elements 30 and 32 in this manner ensures that equivalent amounts of electrical power are supplied to each of the jaw heating elements 30 and 32 despite the jaw heating elements 30 and 32 having different resistance values.

Varying the voltages of the variable voltage power supplies 84 and 86 is not used to regulate the temperature of the jaw heating elements 30 and 32 as part of the temperature feedback control. Instead, the temperatures of the jaw heating elements 30 and 32 are independently regulated by varying the average amount of current supplied to each of the jaw heating elements 30 and 32. The temperature of each of the jaw heating elements 30 and 32 is separately determined from the separately calculated resistance values, as explained above. These calculated temperatures are used in a feedback control algorithm by the control processor 62 to allow individual control over each of the heater power signal 77 and 79 to individually establish, maintain and regulate the temperature of each jaw heating element 30 and 32. Using resistance to temperature data (FIG. 9) that is particular to each jaw heating element 30 and 32 ensures that the derived temperature is accurate, thereby allowing closer regulation of the temperature during the thermal tissue operations.

Positioning the peak voltage detectors 194 and 196 within the handpiece 12 (FIG. 6) close the jaw heating elements 30 and 32 ensures that the voltage sense signals 190 and 192 and the corresponding peak voltage signals 190' and 192' are accurate by avoiding measurements that are degraded by the inherent voltage drop resulting from conducting the current of heater power signals 77 and 79 through the conductors of the cable 28 to the jaw heating elements 30 and 32 of the handpiece 12. Current flowing in a closed circuit path is the same at any point along the path, so the position of the current sensors 166 and 168 at the secondary windings 124 and 126 of the transformers 104 and 106 respectively, accurately represents the amount of current supplied to the jaw heating elements 30 and 32.

Some slight amount of power is inherently consumed by the transformers 104 and 106, so the amount of power delivered to the jaw heating elements 30 and 32 calculated by the control processor 62 in multiplying the peak values 170' and 172' of the secondary current sense signals 170 and 172 by the peak voltage signals 190' and 192' is slightly different from the value of the power calculated by the monitor processor 64 in multiplying the peak values 162' and 164' of the primary current sense signals 162 and 164 by the value of the primary voltage sense signals 96 and 98. Nonetheless, the comparative relationship of the power value calculated by the control processor 62 and the power value calculated by the monitor processor 64 allow the monitor processor 64 to determine whether the control processor 62 is performing appropriately under the circumstances.

The total amount of electrical energy supplied to each jaw heating element since the start of a thermal tissue operation to the end of that thermal tissue operation is calculated by adding the sum of electrical powers calculated multiplied by the time the power is delivered during each control cycle which has occurred since activation of the energy source 26 to accomplish that thermal tissue operation.

Reliable and intended operation of the thermal tissue operating system 10 is confirmed by executing a functional verification test during test intervals between thermal tissue operations, during the course of the entire surgical procedure. The functional verification test is primarily useful for determining the integrity and proper functionality of the jaw heating elements 30 and 32, but may also be useful in determining aspects of proper functionality of the energy source 26 and/or the handpiece 12. The control processor 62 executes the functional verification test and determines whether or not the functional verification test is successful. The monitor processor 64 oversees the timing of each functional verification test performed by the control processor 62. The functional verification test is considered to have failed if the control processor 62 determines that the test has failed. Upon a determination of a failed functional verification test, the monitor processor 60 deactivates the relays 142 and 144 (FIG. 6) to prevent the delivery of the heater power signals 77 and 79 to the jaw heating elements 30 and 32 of the handpiece 12, and/or the control processor 62 deasserts the gate control signals 134 and 136 to the oscillators 128 and 129, and/or the monitor processor 64 deasserts the enable signals 154 and 156 to the oscillators 128 and 129. With the relays 142 and 144 deactivated and/or the oscillators 128 and 129 inoperative, the handpiece 12 can not be used in a surgical procedure. Error messages or other alerts are issued on the display 54 and/or through the speaker 56 (FIG. 1). In this manner, the need to replace or service the energy source 26 or to replace the handpiece 12 is communicated to the user.

Figure 10:
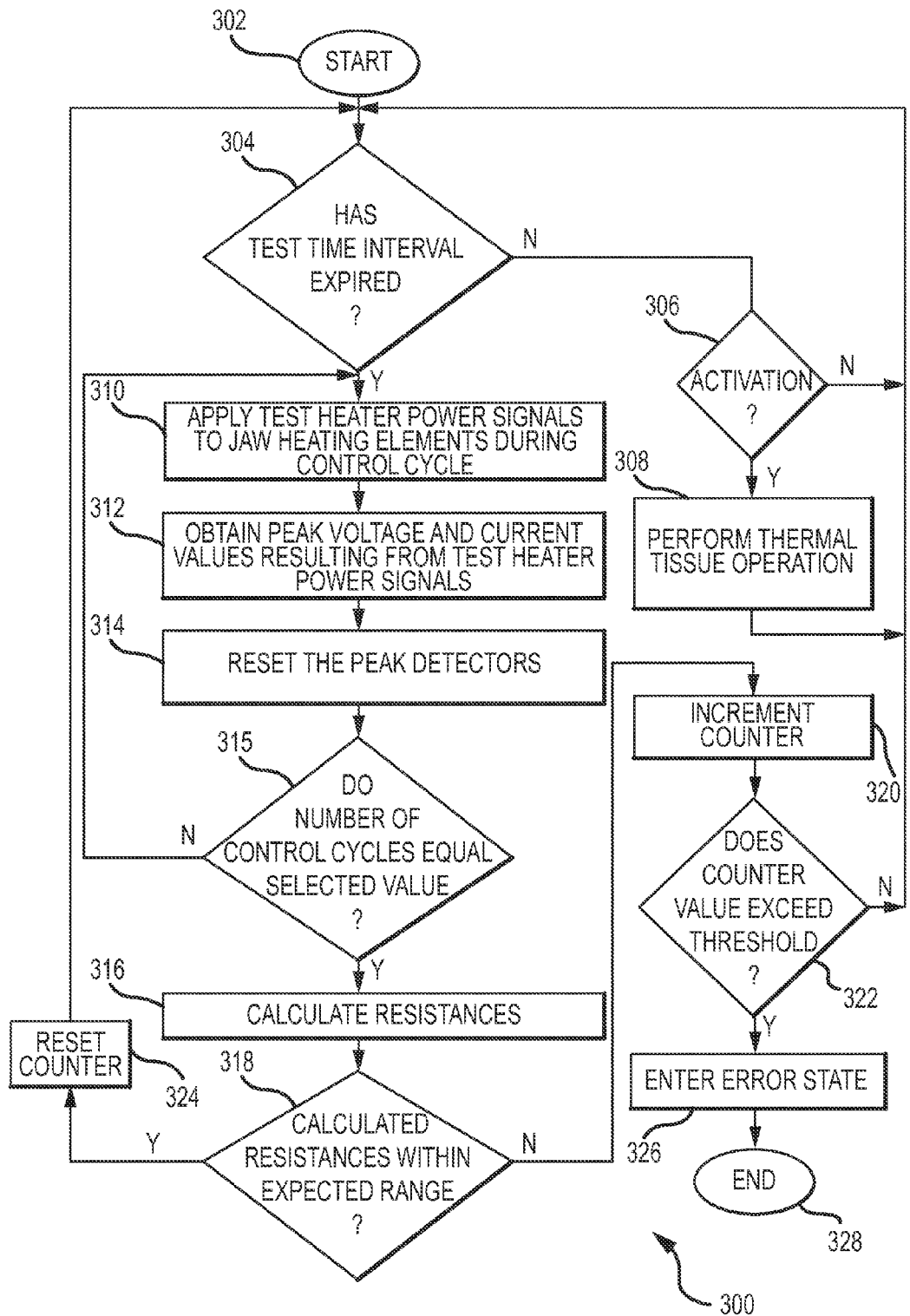
FIG. 10 is a flow chart of a process of conducting a functional verification test of the jaw heating elements and of other functionality of the thermal tissue operating system shown in FIGS. 1-9.

An exemplary process flow 300 of the functional verification test in accordance with the present invention is shown in FIG. 10 and described in conjunction with FIG. 6. The process flow 300 is performed by the control processor 62 in conjunction with the handpiece processor 66, when the tissue fusion system 10 is first started up or powered on, and additionally on a repeating basis between the end of the previous thermal tissue operation and the start of the next subsequent thermal tissue operation during the course of the entire surgical procedure. Each thermal tissue operation is initiated by the user activation signal. In almost every practical application of the thermal tissue operating system, the time between subsequent thermal tissue operations will be more than sufficient to accommodate at least one and typically multiple predetermined test intervals.

Both the control processor 62 and the handpiece processor 66 are programmed to perform their respective parts of the process flow 300 in a coordinated manner. The monitor processor 64 issues an error communication in the event that the control processor 62 performs the functional verification test too frequently and elevates the temperature of the jaw heating elements 30 and 32 beyond a desired level. The monitor processor 64 also issues an error communication in the event that the control processor 62 exceeds a maximum predetermined time to perform one functional verification test. In this manner, the monitor processor 64 oversees the control processor 62 to determine that the execution of the functional verification tests do not occur too frequently or for too long of a time beyond the desired time for a test interval.

The process flow 300 starts at 302. At 304 a determination is made as to whether the functional verification test interval has expired. One purpose of the test interval is to provide an opportunity for the jaw is too cool after performing a thermal tissue operation. An exemplary time for the test interval is approximately 3 seconds. The test time interval can either be fixed in time duration, or it can be variable in time duration in relation to the temperature of the jaw heating elements 30 and 32. For example, the test time interval may be relatively short (approximately 1 second) immediately following a thermal tissue operation, and the jaw heating elements 30 and 32 will still cool. Since the jaw heating elements are already at an elevated temperature immediately following the thermal energy operation, the minimal energy added by the functional verification test does not significantly slow the cooling of the jaws. As the jaw heating elements cool between the subsequent thermal tissue operations, the test time interval can be made longer in duration, since the functional verification test energy has a greater thermal impact when the jaw heating elements 30 and 32 are at a reduced temperature. The test interval should be that amount of time which allows the jaw heating elements to cool between subsequent functional verification tests, so that the jaws do not heat to a potentially injurious temperature from performing the functional verification tests themselves. Affording the jaw heating elements 30 and 32 an opportunity to cool between iterations of the functional verification test prevents the jaw heating elements 30 and 32 from reaching elevated temperatures sufficient to injure the surgeon or surgical personnel due to accidental contact with the jaws 14 and 16 (FIG. 1).

If the determination at 304 is negative, the process flow 300 continues at 306. A determination is made, at 306, as to whether an activation signal has been received by the control processor 62. If the determination at 306 is affirmative, then a thermal tissue operation (FIGS. 2, 3 and 4) is performed at 308 without performing the functional verification test. If the determination at 306 is negative, or after the thermal tissue operation has been performed at 308, the process flow 300 returns to 304. So long as the determinations at 304 and 306 are negative, the process flow 300 loops between the determinations at 304 and 306 until the functional verification test time interval has expired.

When the determination at 304 is affirmative after expiration of the functional verification test time interval, the process flow 300 continues to 310. At 310, the control processor 62 asserts the gate control signals 134 and 136 to the oscillators 128 and 129 while the monitor processor 64 asserts the enable signals 154 and 156 to enable the oscillators 128 and 129. The monitor processor 64 also asserts the relay activation signals 146 and 148 to the relays 142 and 144, causing test heater power signals 77 and 79 to be supplied to the jaw heating elements 30 and 32. The control processor 62 supplies the gate control signals 134 and 136 at a low power test duty cycle for a predetermined number of control cycles 104 (FIGS. 7A-7H, 8A-8C), to create the low power test heater power signals 77 and 79 that are supplied to the jaw heating elements 30 and 32.

The amount of power delivered for each test heater power signal is a finite amount greater than zero, and is equal to or preferably somewhat less than the minimum amount of power delivered to the jaw heating elements during a normal thermal tissue operation. The test heater power signals 77 and 79 used in the functional verification test are supplied for a relatively few number of control cycles 104 (FIGS. 7A-7H, 8A-8C). The relatively low power and fewer number of control cycles of the test heater power signals minimize the extent to which the jaw heating elements 30 and 32 increase in temperature, but nevertheless increase the temperature of the jaw heating elements enough for evaluation during the functional verification test.

At 312, the control processor 62 obtains the peak values 170' and 172' from the peak current detectors 178 and 180 while the test heater power signals are applied at 310. Also at 312, the control processor 62 obtains peak values 190' and 192' from the peak voltage detectors 194 and 196. The handpiece processor 66 sends the peak voltage values 190' and 192' to the control processor 62 over the communication bus 68.

At 314, the peak current detectors 178 and 180 and the peak voltage detectors 194 and 196 are reset. The control processor 62 resets the peak current detectors 178 and 180 by asserting the reset signal 184. The control processor 62 also sends to the handpiece processor 66 a reset command, and in response, the handpiece processor 66 asserts the reset signal 198 to reset the peak voltage detectors 194 and 196.

At 315, a determination is made of the number of control cycles 104 (FIGS. 7A-7H, 8A-8C). It has been determined that a number, for example four, control cycles of applying the test heater power signals 77 and 79 to the jaw heating elements 30 and 32 allows the components of the peak detectors to obtain a more accurate ending value than the values obtained immediately upon initiation of the test time interval. The determination at 315 allows the predetermined number of control cycles 104 to occur before the final values of the peak voltage and peak current are obtained. The final values of the peak voltage and the peak current obtained from the last control cycle are retained for use in calculating the resistance before the peak detectors are reset at 314. Until the last control cycle of applying the test heater power signals occurs, the determination at 315 will be negative, causing the test heater power signals to be applied during next control cycle of the test interval at 310.

An affirmative determination at 315 allows the control processor 62 to calculate the resistance values for each of the jaw heating elements 30 and 32 at 316. The resistance values are calculated from the peak voltage and current values obtained from the last control cycle of the test interval by dividing the peak voltage values 190' and 192' by the peak current values 170' and 172'.

At 318, the control processor 62 determines whether or not each of the resistances calculated at 316 is within predefined range of expected resistances. The range of expected resistances accounts for normal variations in the resistances of jaw heating elements of many different handpieces 12 used with the energy source 26. The range of expected resistances are recorded in the memory 73 of the control processor 62.

A calculated resistance which is above the high value of the expected range indicates a diminishing cross-sectional size of a jaw heating element, or an open circuit condition, or an infinite or extremely high resistance. An extremely high resistance or open circuit will cause considerably less than the expected current to flow to the jaw heating elements 30 and 32, resulting in substantially reduced thermal energy available for delivery to the tissue. A calculated resistance which is below the low value of the expected range indicates increased conductivity or a short circuit. A short circuit could result from the heat of a jaw heating element melting insulation material around the conductors supplying current to the jaw heating element. A very high conductivity (low resistance) or short circuit will cause the jaw heating elements to deliver reduced or minimal thermal energy to the tissue, and may overload the current conducting capability of certain elements in the energy source 26. In these abnormal circumstances, the calculated resistance of a jaw heating element falls outside of the expected resistance range, and the abnormal resistance will adversely affect the amount of power delivered, the capability to regulate the temperature, and the quality or integrity of the thermal tissue operation performed.

A negative determination at 318 indicates that at least one of the calculated resistances is not within the expected range of resistances. Under such circumstances, the process flow 300 then continues to 320 where a counter is incremented. The count value which is incremented at 320 represents the number of times where at least one of the calculated resistances is not within the expected range during each test interval, as indicated by a negative determination at 318. An error will be indicated upon at least one of the calculated resistances falling outside of the expected range on a consistent basis for a predetermined number of sequential test intervals. The counter value which is incremented at 320 represents the number of sequential test intervals where at least one of the calculated resistances was not within the expected range.

At 322, a determination is made as to whether the count value exceeds a threshold. The threshold represents the number of sequential test time intervals that at least one of the calculated resistances was not within the expected range during sequential test intervals. The threshold represented at 322 therefore establishes the error condition. As an example, the threshold value represented at 322 may be three sequential test intervals.

A negative determination at 322 causes the process flow 300 to revert back to 304 to start the execution of another functional verification test during another time interval using the previously described process flow 300. If the determination at 318 is affirmative, indicating that the calculated resistance value shows that both jaw heating elements have functionally acceptable resistance values, the counter value is reset to zero at 324. One instance of the functional verification test demonstrating that both jaw heating elements have functionally acceptable resistance values eliminates the possibility of reaching the threshold number of negative determinations at 318. Accordingly, resetting the counter value at 324 readies the counter to again increment and count the number of instances where at least one of the calculated resistances of the jaw heating elements is outside of the expected range, as determined by a negative determination at 318. So long as the counter is reset at 324 before the threshold determined at 322 is reached, a continuous sequence of test intervals governed by the threshold at 322 must occur during which at least one calculated resistance of the jaw heating elements falling outside of the expected range.

An affirmative determination at 322 results in the control processor 322 entering an error state at 326. The error state is communicated to the monitor processor 64 over the bus 70. An error message is presented on the display 54 (FIG. 1), and/or an audible error message is delivered through the speaker 56 (FIG. 1), to indicate a problem with at least one of the jaw heating elements 30 and 32. Either or both of the control processor 62 and monitor processor 64 prevent the use of the tissue fusion system 10 when the control processor 62 is in the error state at 326. The process flow 300 ends at 328 after entering the error state at 326. The error state at 326 is exited when a different handpiece 12 is connected to the energy source 26.

If a malfunction occurs in the current sensors 166 and 168, or in the peak current detectors 178 and 180, or in the peak voltage detectors 194 and 196, those problems will manifest themselves in inaccurate values of the quantities sensed and detected. Similarly a malfunction in the resistance calculation functionality executed by the control processor will also manifest itself as an inaccurate value of the calculated resistance. Under these circumstances, even if the actual resistance characteristics of the jaw heating elements 30 and 32 are acceptable, the resistance values calculated at 316 will be based on inaccurate values and are likely to cause a failed functional verification test. Under such circumstances, the process flow 300 will enter the error state 326, and further use of the thermal tissue operating system 10 is prevented. Thus in this manner, certain aspects of the proper functionality of the handpiece 12 and the energy source 26 are continually evaluated and verified on an ongoing basis between thermal tissue operations of the surgical procedure.

Performing the functional verification test according to the process flow 300 detects problems with the thermal tissue operating system 10 that might otherwise go unnoticed until after a number of compromised thermal tissue operations have been performed. Detecting problems with the jaw heating elements, or the functionality of the handpiece 12 and the energy source 26, by execution of the process flow 300 helps to reduce or eliminate the possibility of complications and excessive patient trauma.

These and other improvements and advantages will be more apparent after comprehending the full ramifications of the present invention. Presently preferred embodiments of the present invention and many of its improvements have been described with a degree of particularity. This description is of preferred examples of implementing the invention, and is not necessarily intended to limit the scope of the invention. The scope of the invention is defined by the following claims.

What is claimed:

1. A thermal tissue operating system for performing thermal tissue operations during a surgical procedure, the thermal tissue operating system including an energy source and a handpiece connected to the energy source, the handpiece including a first jaw and a second jaw configured to compress tissue therebetween during the thermal tissue operation, the first jaw including a first jaw heating element and the second jaw including a second jaw heating element for converting electrical power to thermal heat energy, the energy source configured to supply a heater power signal having voltage and current to the first jaw heating element and the second jaw heating element, wherein the energy source comprises:
  a controller programmed to control delivery of the heater power signal to the first jaw heating element and the second jaw heating element;
  a first voltage sensor configured to sense the voltage of the heater power signal supplied to the first jaw heating element and configured to supply a first voltage sense signal in response;
  a second voltage sensor configured to sense the voltage of the heater power signal supplied to the second jaw heating element and configured to supply a second voltage sense signal in response;
  a first current sensor configured to sense the current of the heater power signal supplied to the first jaw heating element and configured to supply a first current sense signal in response;
  a second current sensor configured to sense the current of the heater power signal supplied to the second jaw heating element and configured to supply a second current sense signal in response; and wherein:
  the controller is programmed to calculate a first resistance value of the first jaw heating element and to compare the calculated first resistance value to a predetermined range of expected resistance values for the first jaw heating element based on the first voltage sense signal and the first current sense signal;

the controller is programmed to calculate a second resistance value of the second jaw heating element and to compare the calculated second resistance value to a predetermined range of expected resistance values for the second jaw heating element based on the second voltage sense signal and the second current sense signal;

the controller is programmed to respond to an activation signal, which is an indication of an execution of a thermal tissue operation, to supply the heater power signal as an operational heater power signal having sufficient energy to accomplish the thermal tissue operation;

the controller is programmed to respond to an absence of the activation signal between any subsequent thermal tissue operations to supply the heater power signal as a test heater power signal during a predetermined test interval, the test heater power signal having insufficient energy to accomplish a thermal tissue operation but having sufficient energy to create the first and second voltage sense signals and the first and second current sense signals to enable the controller to calculate the first and second resistance values of the first and second jaw heating elements;

the first voltage sensor and the first current sensor are configured to sense the voltage and current of the test heater power signal supplied to the first jaw heating element;

the second voltage sensor and the second current sensor are configured to sense the voltage and the current of the test heater power signal supplied to the second jaw heating element;

the controller is programmed to signal an error state and prevent further delivery of the operational heater power signals to the first and second jaw heating elements when at least one of the calculated first and second resistance values falls outside of the predetermined range of expected resistance values;

the controller comprises a control processor which is part of the energy source and a handpiece processor which is part of the handpiece; and the handpiece processor is programmed to determine the voltage across the first and second jaw heating elements and to communicate the determined voltages to the control processor as the first and second voltage sense signals.

2. The thermal tissue operating system as defined in claim 1, further comprising:

a first and second peak voltage detectors within the handpiece for sensing the voltage of the first and second jaw heating elements and supplying a peak voltage signal for each of the first and second jaw heating elements that indicate a peak magnitude of the sensed voltages across each of the first and second jaw heating elements during each test interval; and wherein:

the handpiece processor communicates the peak voltages to the control processor as the first and second voltage sense signals.

3. The thermal tissue operating system as defined in claim 1, wherein:

each of the first and second peak voltage detectors is operative over a sample time interval to detect and hold the peak voltage signal of the sensed voltages over the sample time interval; and the calculation of the first and second resistance values are performed using a maximum value of the voltage and current during each test interval.

\* \* \* \* \*